(12) United States Patent
Scheule et al.

(10) Patent No.: US 11,253,683 B2
(45) Date of Patent: Feb. 22, 2022

(54) METHOD AND APPARATUS FOR TREATING ASCITES

(71) Applicant: ewimed, Hechingen-Boll (DE)

(72) Inventors: Albertus Scheule, Tübingen (DE); Egon Wiest, Hechingen (DE)

(73) Assignee: ewimed, Hechingen-Boll (DE)

( * ) Notice: Subject to any disclaimer, the term of this patent is extended or adjusted under 35 U.S.C. 154(b) by 1072 days.

(21) Appl. No.: 15/426,184

(22) Filed: Feb. 7, 2017

(65) Prior Publication Data
US 2018/0221632 A1    Aug. 9, 2018

(51) Int. Cl.
*A61M 27/00*    (2006.01)

(52) U.S. Cl.
CPC ........... *A61M 27/002* (2013.01); *A61M 27/00* (2013.01)

(58) Field of Classification Search
CPC .............................. A61M 27/002; A61M 27/00
USPC ............................................................ 604/9
See application file for complete search history.

(56) References Cited

U.S. PATENT DOCUMENTS

| 5,839,172 A * | 11/1998 | Takizawa | A44B 18/0061 |
| | | | 24/452 |
| 2013/0325103 A1* | 12/2013 | Arai | A61F 2/2418 |
| | | | 623/1.24 |
| 2017/0304597 A1* | 10/2017 | Forsell | A61M 1/1008 |

FOREIGN PATENT DOCUMENTS

WO    WO 97/20584    6/1997

* cited by examiner

*Primary Examiner* — Andrew J Mensh
(74) *Attorney, Agent, or Firm* — Pandiscio & Pandiscio

(57) ABSTRACT

A valve for treating ascites, the valve comprising: a body having a distal end, a proximal end and a lumen extending therebetween; at least one valve element disposed in the lumen of the body, the at least one valve element being a one-way valve element configured to permit the passage of fluid in a single direction through the lumen of the body; and at least one connection element provided on at least one of the distal end and the proximal end of the body, wherein the at least one connection element is configured to connect the body of the valve to the side wall of a blood vessel.

7 Claims, 34 Drawing Sheets

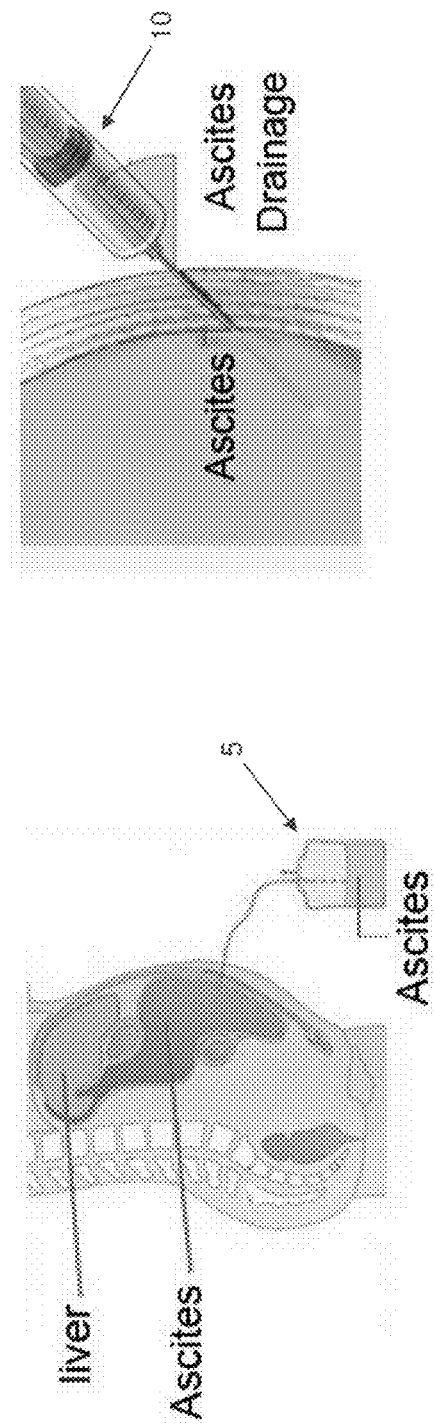
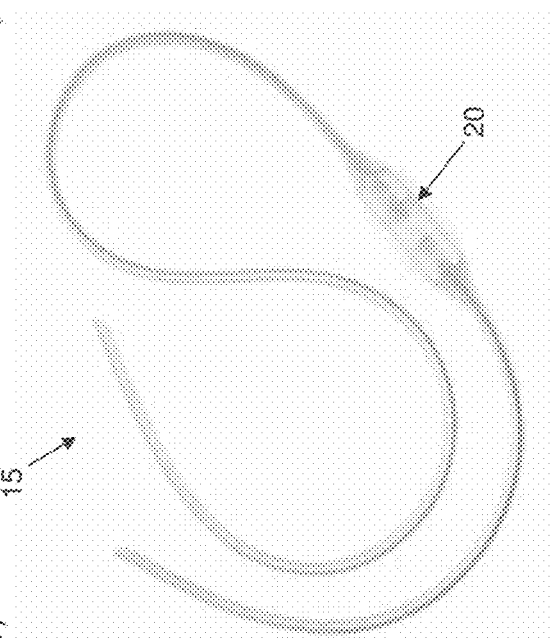
FIG. 1 (PRIOR ART)
FIG. 2 (PRIOR ART)
FIG. 3 (PRIOR ART)

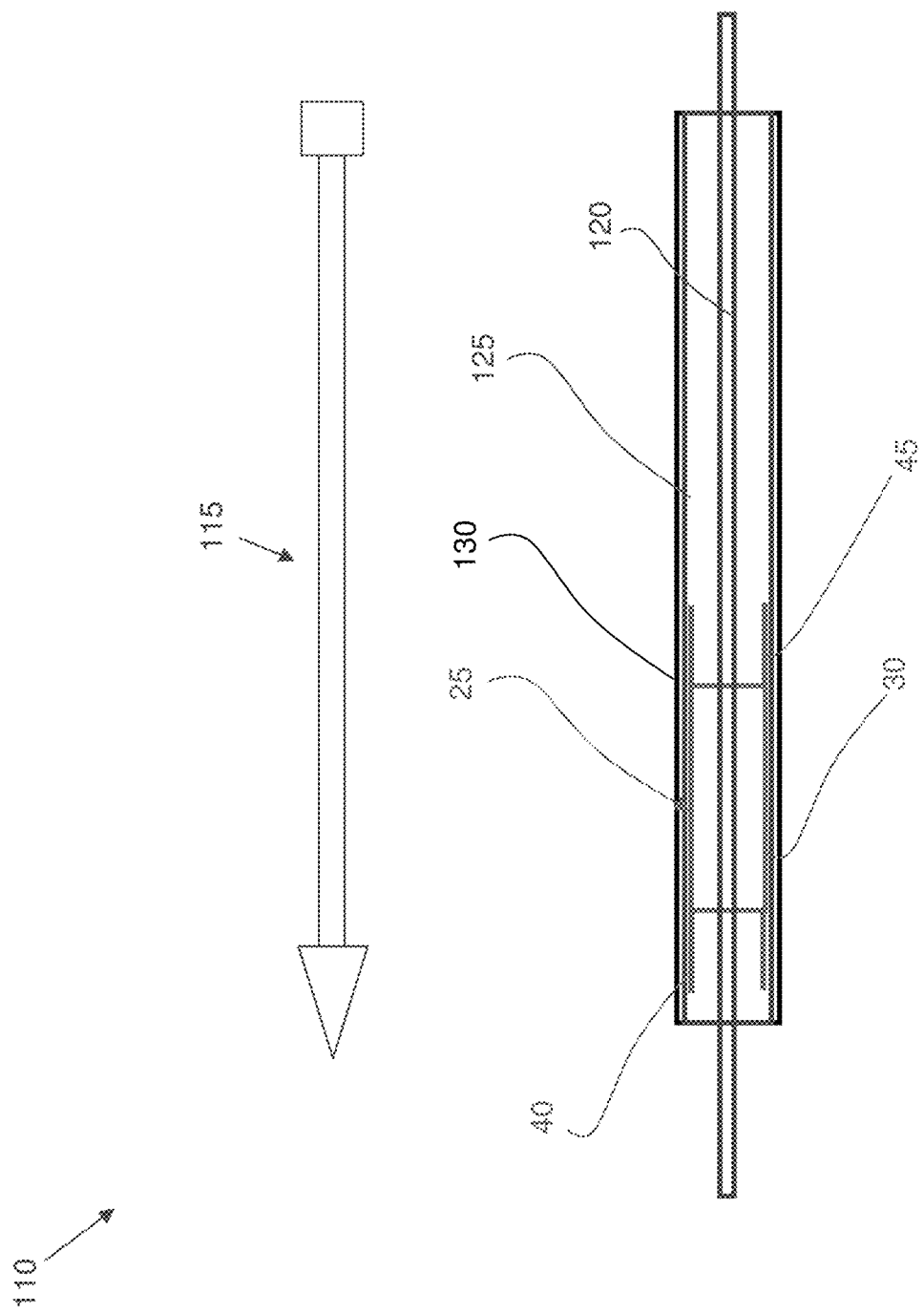

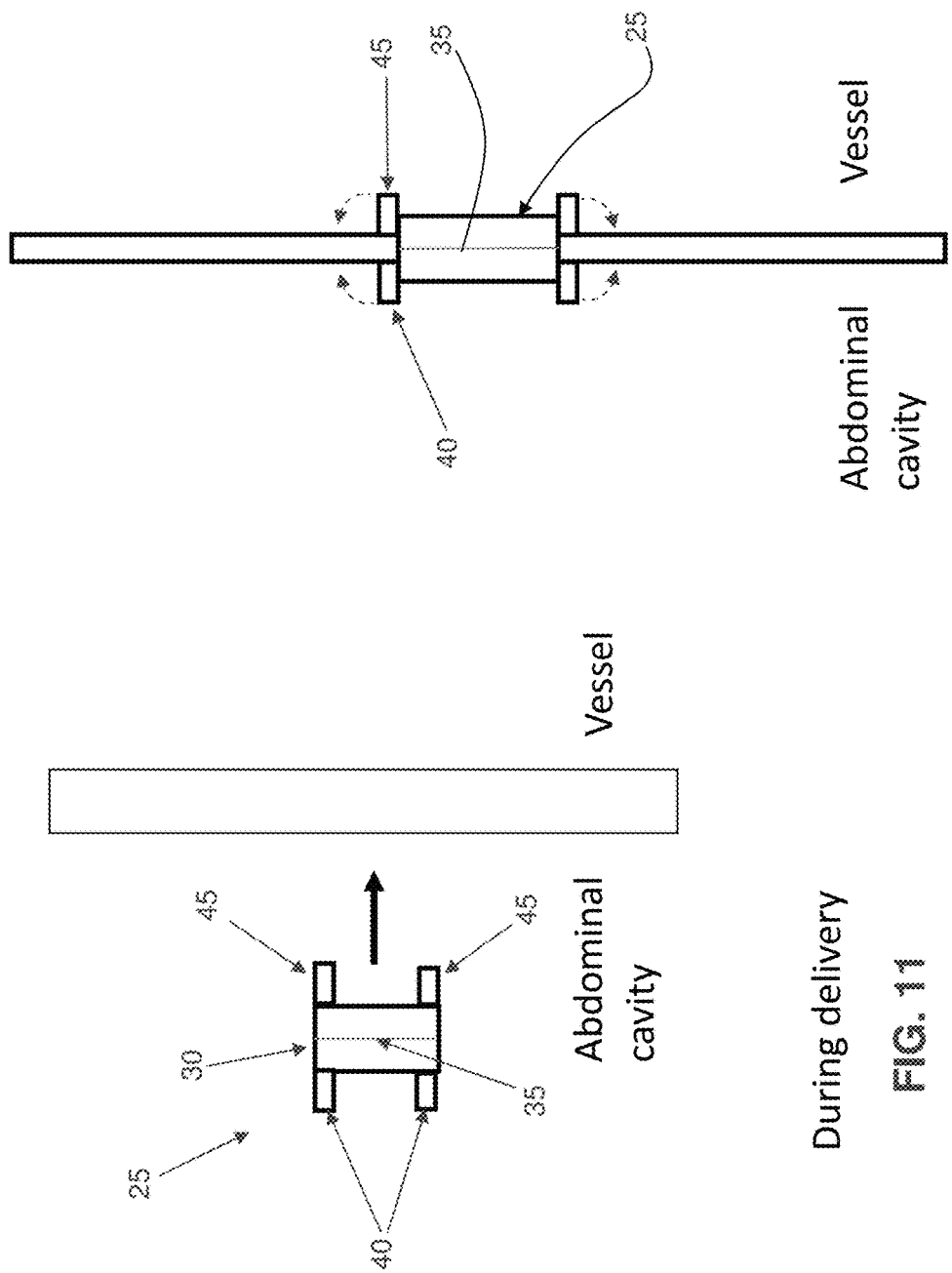

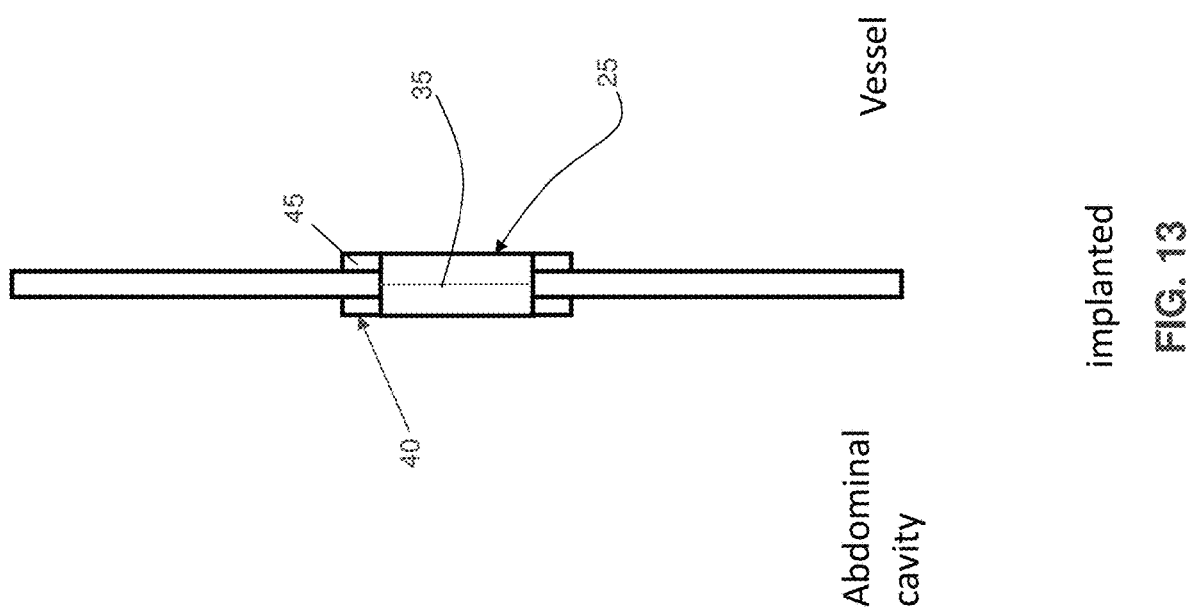

implanted

Placement of the device

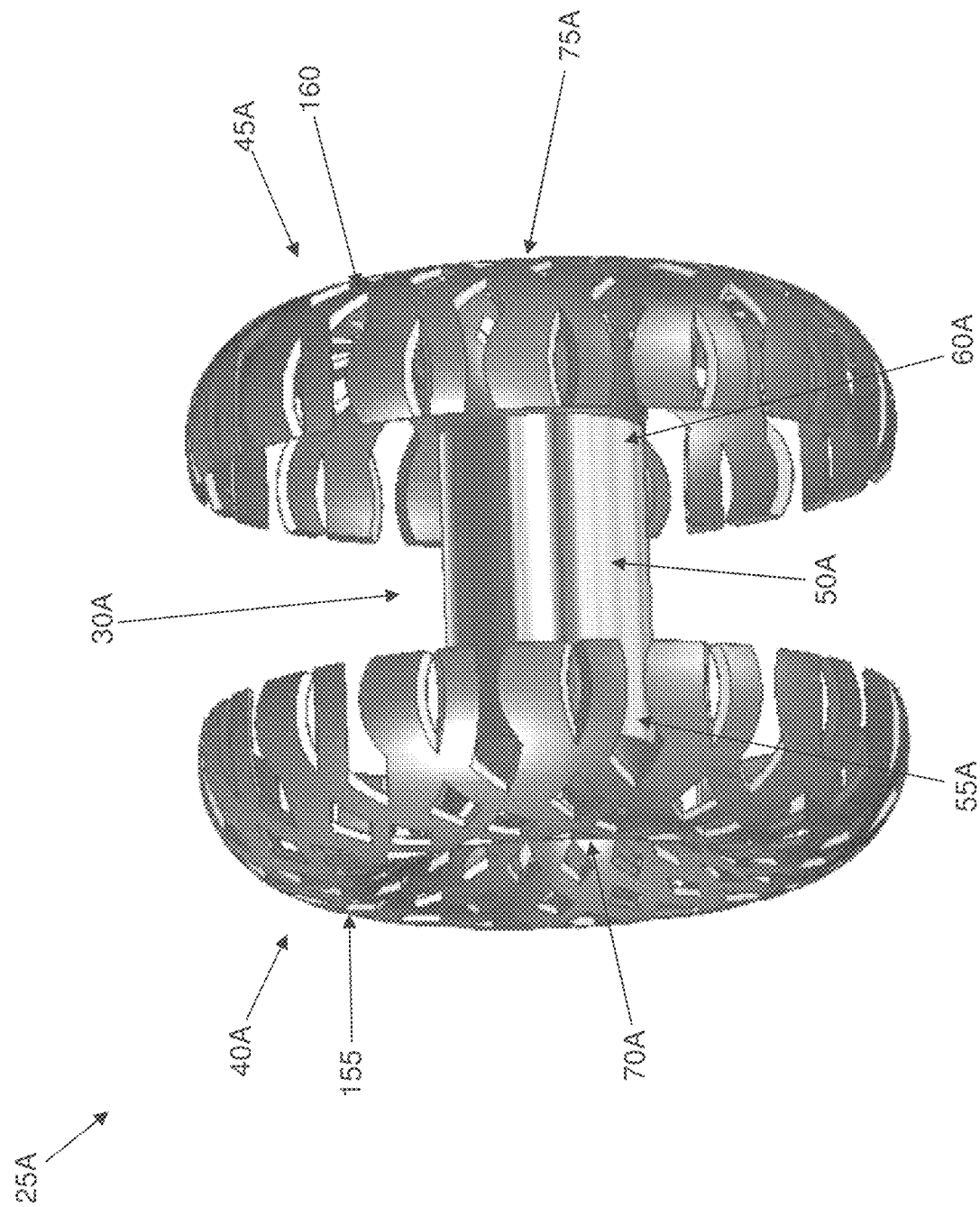

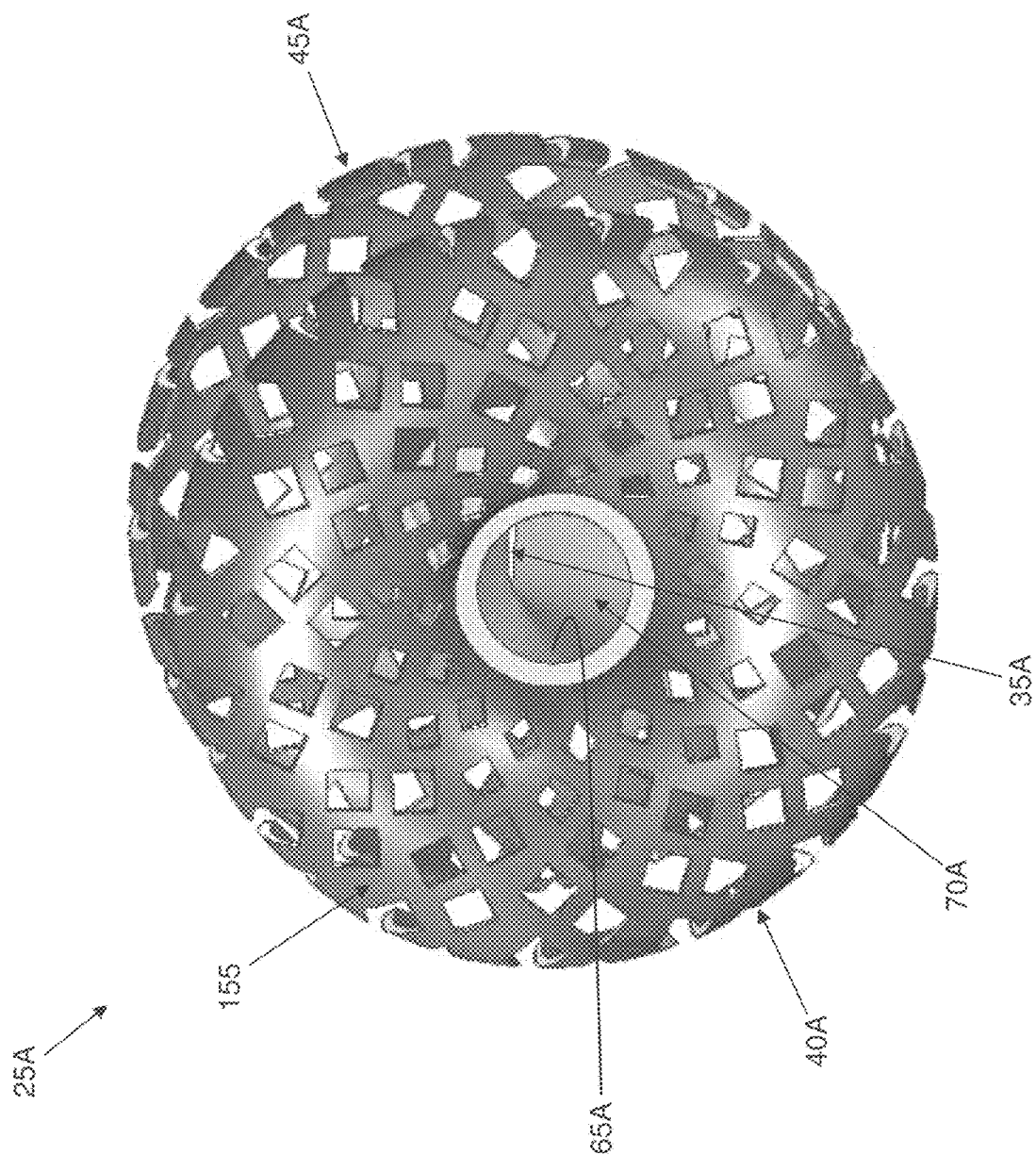

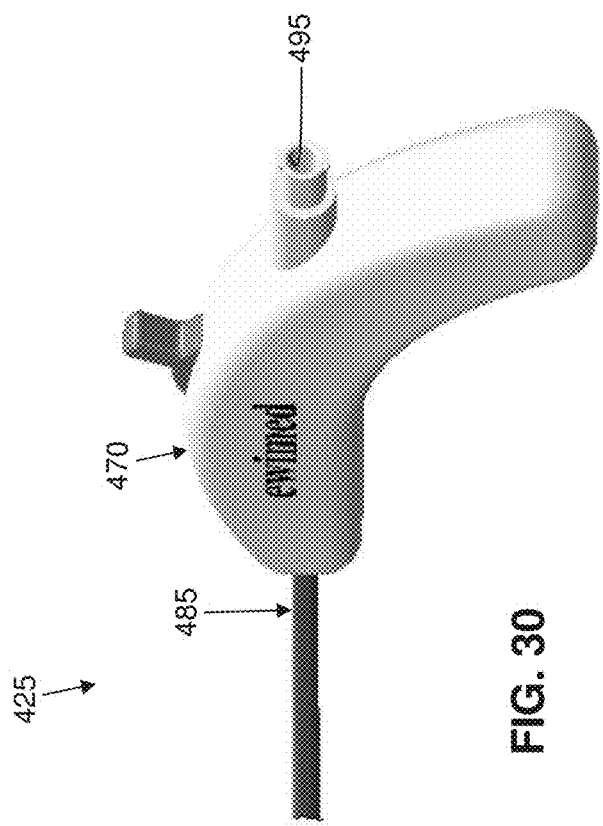
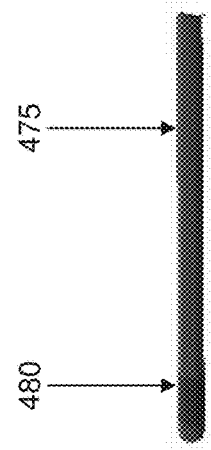
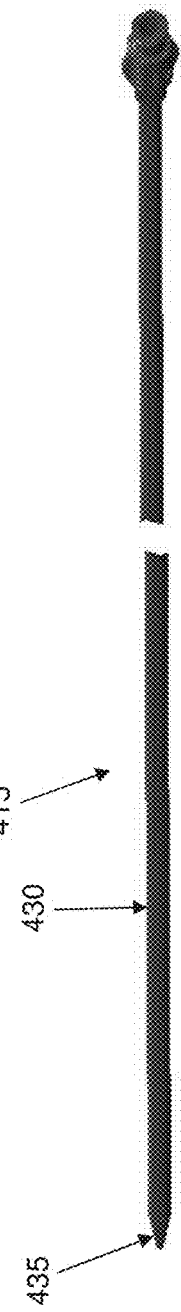
FIG. 30
FIG. 31
FIG. 32

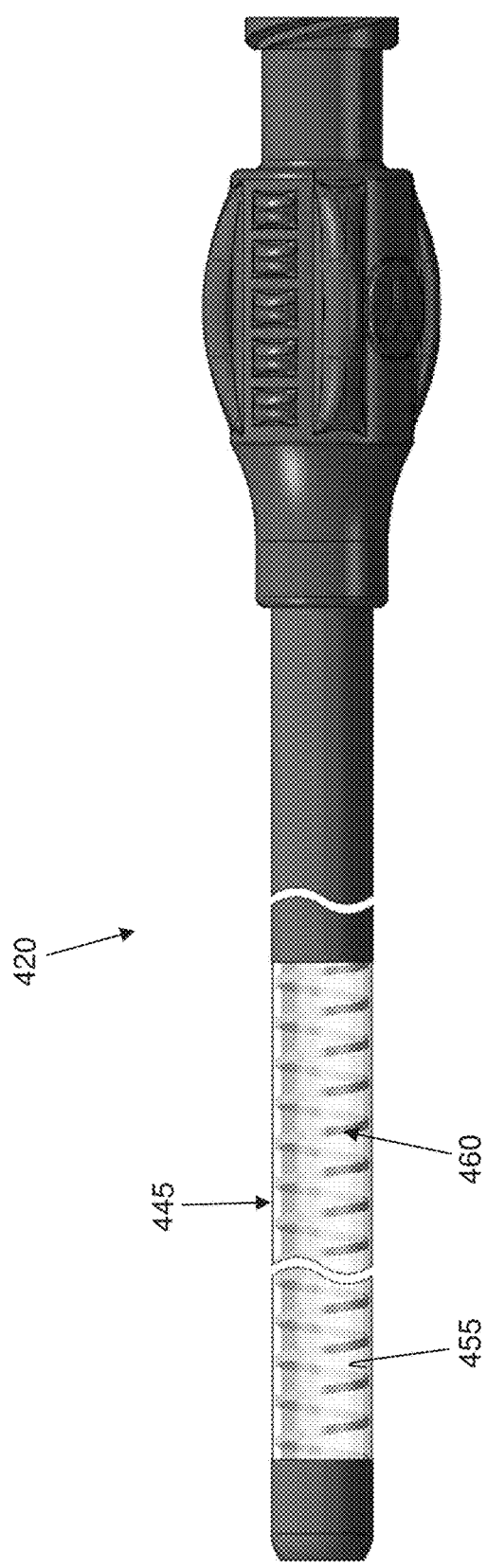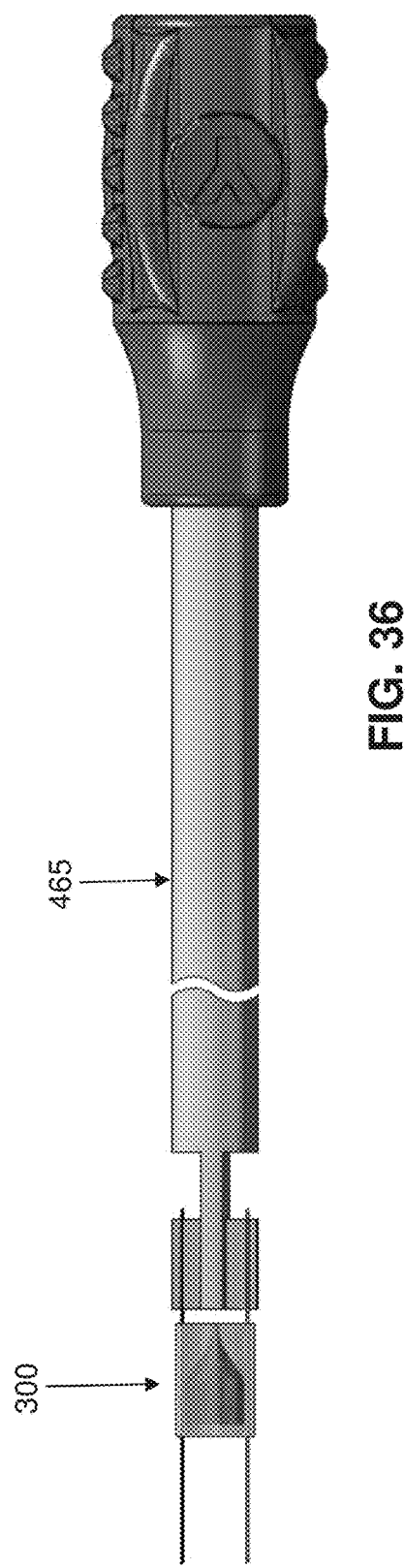

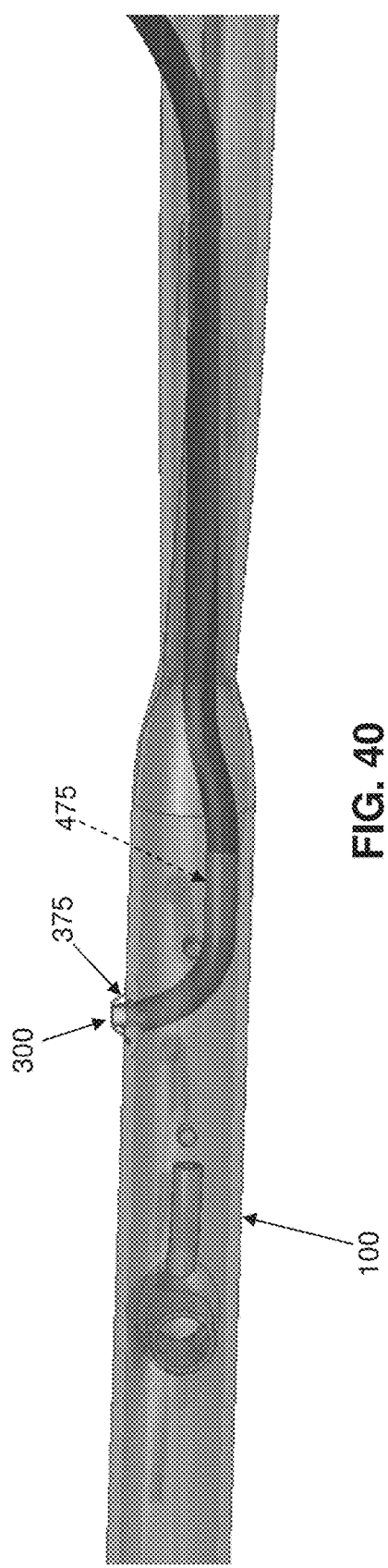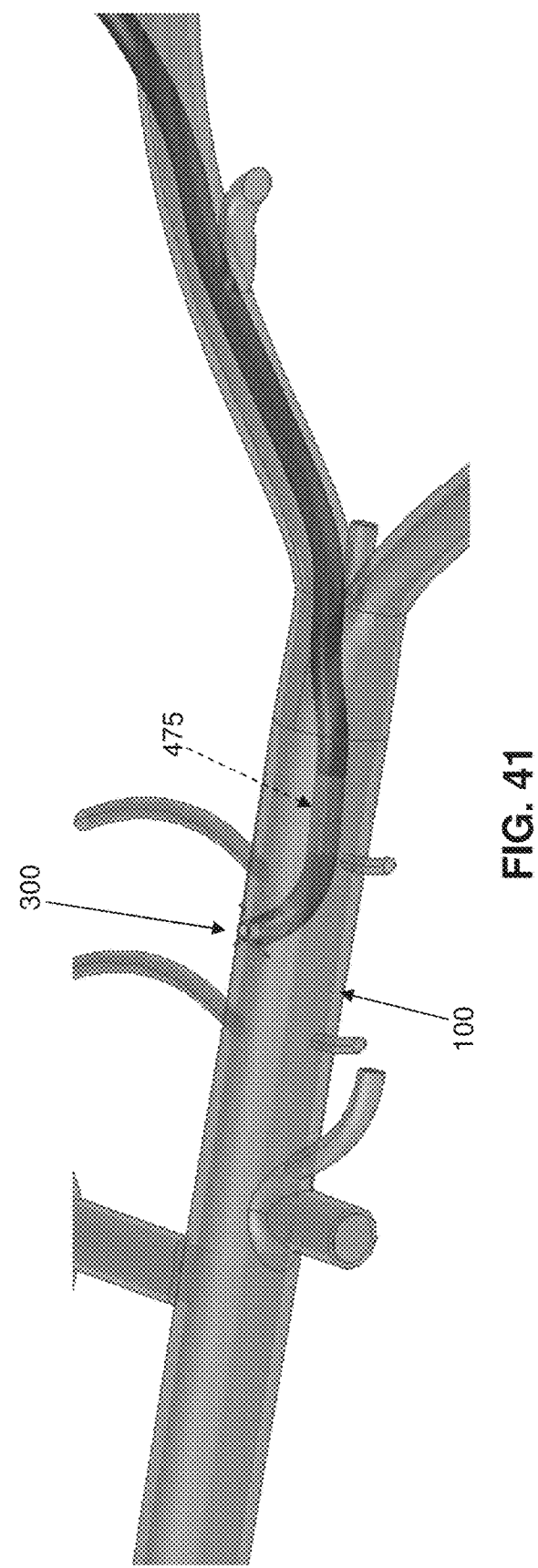

METHOD AND APPARATUS FOR TREATING ASCITES

FIELD OF THE INVENTION

The present invention relates to methods and apparatus for treating medical conditions in general, and more particularly to a novel method and apparatus for treating ascites.

BACKGROUND OF THE INVENTION

Ascites is the condition of pathologic fluid collection within the abdominal cavity, in particular within the peritoneal cavity. Ascites can be caused by different diseases, e.g., cirrhosis, cancer and heart failure, among other diseases.

One way of treating ascites is by the direct removal of the excess fluid from the abdominal cavity. Such direct removal is typically effected by puncturing the abdominal wall (e.g., with a needle) and using a pump (e.g., a syringe) to generate suction to remove the fluid from the body. See, for example, FIG. 1, which shows direct removal of excess fluid from the abdominal cavity via drainage to a collection bag 5; and FIG. 2, which shows direct removal of excess fluid from the abdominal cavity using a syringe 10. Inasmuch as the excess fluid removed from the body typically contains important biological components which should not be discarded, the fluid that is removed from the body may thereafter be re-introduced into the body at a different location, e.g., the jugular vein. Since excess fluid may build up again in the abdominal cavity even after removal of fluid, repetition of the removal and re-introduction procedure may be necessary.

In order to decrease the burden on the patient (i.e., the burden resulting from continued invasive procedures which are needed in order to access the abdominal cavity to remove fluid and to re-introduce the fluid into the body at a different location), shunts may be implanted into the body of the patient to connect the peritoneal cavity with the major thoracic vein via flexible tubing. See, for example, FIGS. 3 and 4, which show an exemplary catheter 15 which may be used as a shunt. A one-way valve 20 is typically provided in catheter 15 in order to control the direction of fluid flow (i.e., to allow the fluid to flow in only one direction, from the abdominal cavity to the thoracic vein). Such shunts are commonly referred to as peritoneovenous (or "P-V") shunts. The one-way fluid flow through a P-V shunt is typically caused by pressure which is generated during respiration (i.e., when mechanical impingement of the diaphragm on the ascetic fluid pressurizes the fluid, causing the fluid to flow into the P-V shunt). Most of the ascetic fluid which is introduced into the major thoracic vein is ultimately excreted from the body as urine, while plasma proteins which are present in the ascetic fluid are retained in the blood.

By way of example but not limitation, EP 0 806 970 A1 shows an improved valve which may be used in a typical P-V shunt. However, the valve of EP 0 806 970 A1 is positioned between the peritoneal tubing of the P-V shunt and the venous tubing of the P-V shunt. As a result, with such a valve, there is a significant risk of the failure of the P-V shunt due to blocking of the peritoneal tubing (and possibly also the venous tubing) by the pressure created against the tubing in the abdominal cavity. In addition, the long distance traversed by the P-V shunt (i.e., the distance from the patient's abdominal cavity to the patient's major thoracic vein) requires a long shunt and an invasive procedure to implant the shunt in the patient's body.

Thus there is a need for a new and improved method and apparatus for the treatment of ascites which eliminates the problems encountered when using long shunts, which allows for the recirculation of ascetic fluid without removing it from the patient's body, and which places as little burden on the patient as possible.

SUMMARY OF THE INVENTION

The present invention eliminates the need for long shunts, and the burden imposed on the patient by implanting long shunts within the patient's body, while avoiding the need to remove fluid from, and re-introduce fluid into, the patient's body. As a result, the present invention is able to significantly reduce the burden on the patient which is typically encountered when using traditional P-V shunts (e.g., resistance to fluid flow and higher occlusion rates).

More particularly, the present invention comprises the provision and use of a novel implantable one-way valve, and a method for treating a patient using the novel implantable one-way valve, so as to provide a direct connection between the abdominal cavity and the venous system of the patient.

In one preferred form of the present invention, there is provided a valve for treating ascites, the valve comprising:

a body having a distal end, a proximal end and a lumen extending therebetween;

at least one valve element disposed in the lumen of the body, the at least one valve element being a one-way valve element configured to permit the passage of fluid in a single direction through the lumen of the body; and at least one connection element provided on at least one of the distal end and the proximal end of the body, wherein the at least one connection element is configured to connect the body of the valve to the side wall of a blood vessel.

In another preferred form of the present invention, there is provided a method of treating ascites, the method comprising:

implanting a one-way valve into the side wall of a blood vessel located adjacent the abdominal cavity, so that one side of the valve lies within, and is fluidically connected to, the abdominal cavity and the other side of the valve lies within, and is fluidically connected to, the interior of the blood vessel.

In another preferred form of the present invention, there is provided a valve for treating ascites, the valve comprising:

a body having a distal end, a proximal end and a lumen extending therebetween;

at least one valve element mounted to the distal end of the body and extending distally therefrom, the at least one valve element being a one-way valve element configured to permit the passage of fluid in a single direction through the lumen of the body; and at least one connection element provided on at least one of the distal end and the proximal end of the body, wherein the at least one connection element is configured to connect the body of the valve to the side wall of a blood vessel.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 1 is a schematic view showing how ascetic fluid may be removed from the abdomen of a patient using a drainage bag;

FIG. 2 is a schematic view showing how ascetic fluid may be removed from the abdomen of a patient using a syringe;

FIGS. 3 and 4 are schematic views of a prior art P-V shunt which may be used to remove fluid from the abdomen of a patient and re-introduce the fluid into the patient at a remote location;

FIG. 10 is a schematic view showing a novel delivery system which may be used to deliver a novel one-way valve to an internal anatomical site;

FIGS. 11-13 are schematic views showing how a novel one-way valve formed in accordance with the present invention may be implanted into the side wall of a blood vessel using an "abdominal approach";

FIGS. 16-18 are schematic views showing another novel one-way valve formed in accordance with the present invention;

FIGS. 29-36 are schematic views showing another novel delivery system which may be used to deliver a novel one-way valve (e.g., the novel one-way valve of FIGS. 27 and 28) to an internal anatomical site; and FIGS. 37-42 are schematic views showing how a novel one-way valve (e.g., the novel one-way valve of FIGS. 27 and 28) formed in accordance with the present invention may be implanted into the side wall of a blood vessel via an "endovascular approach" using the novel delivery system of FIGS. 29-36.

DETAILED DESCRIPTION OF THE PREFERRED EMBODIMENTS

Figure 4:
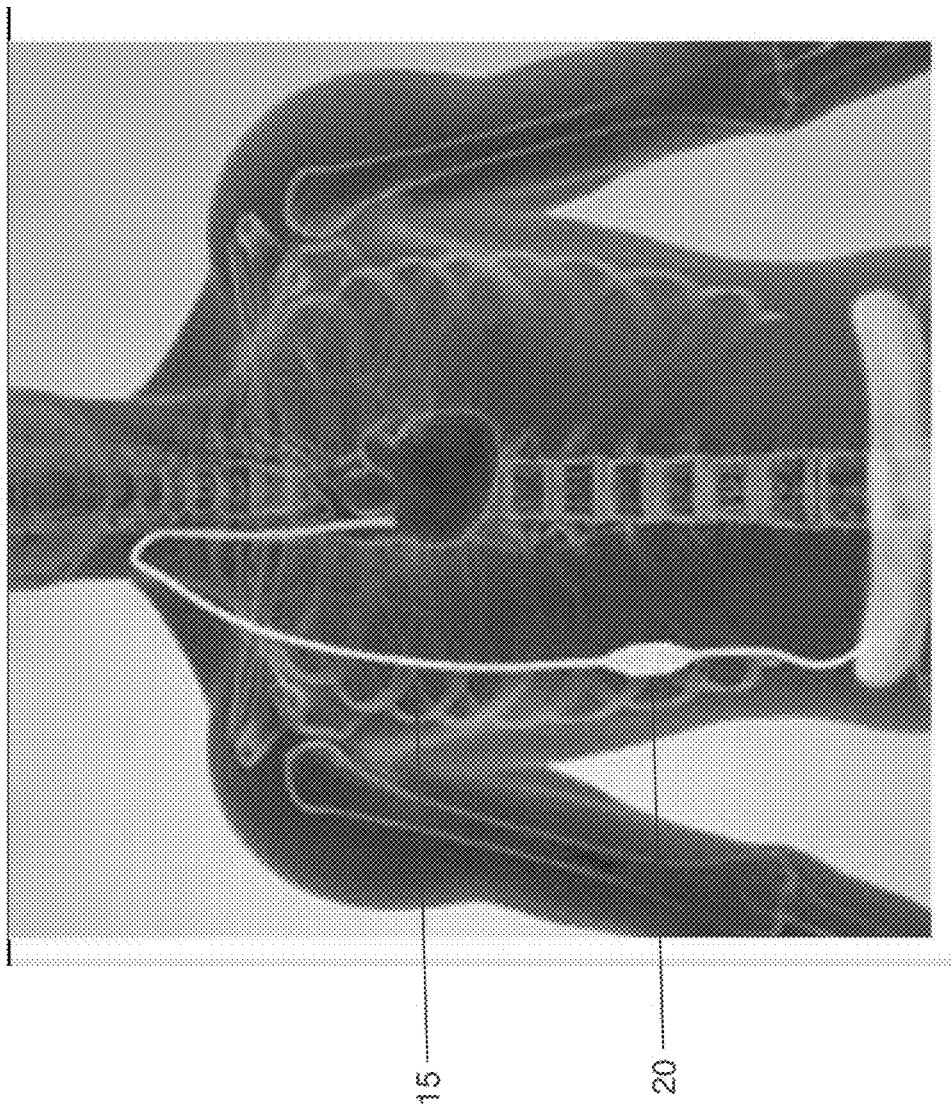
Figure 5:
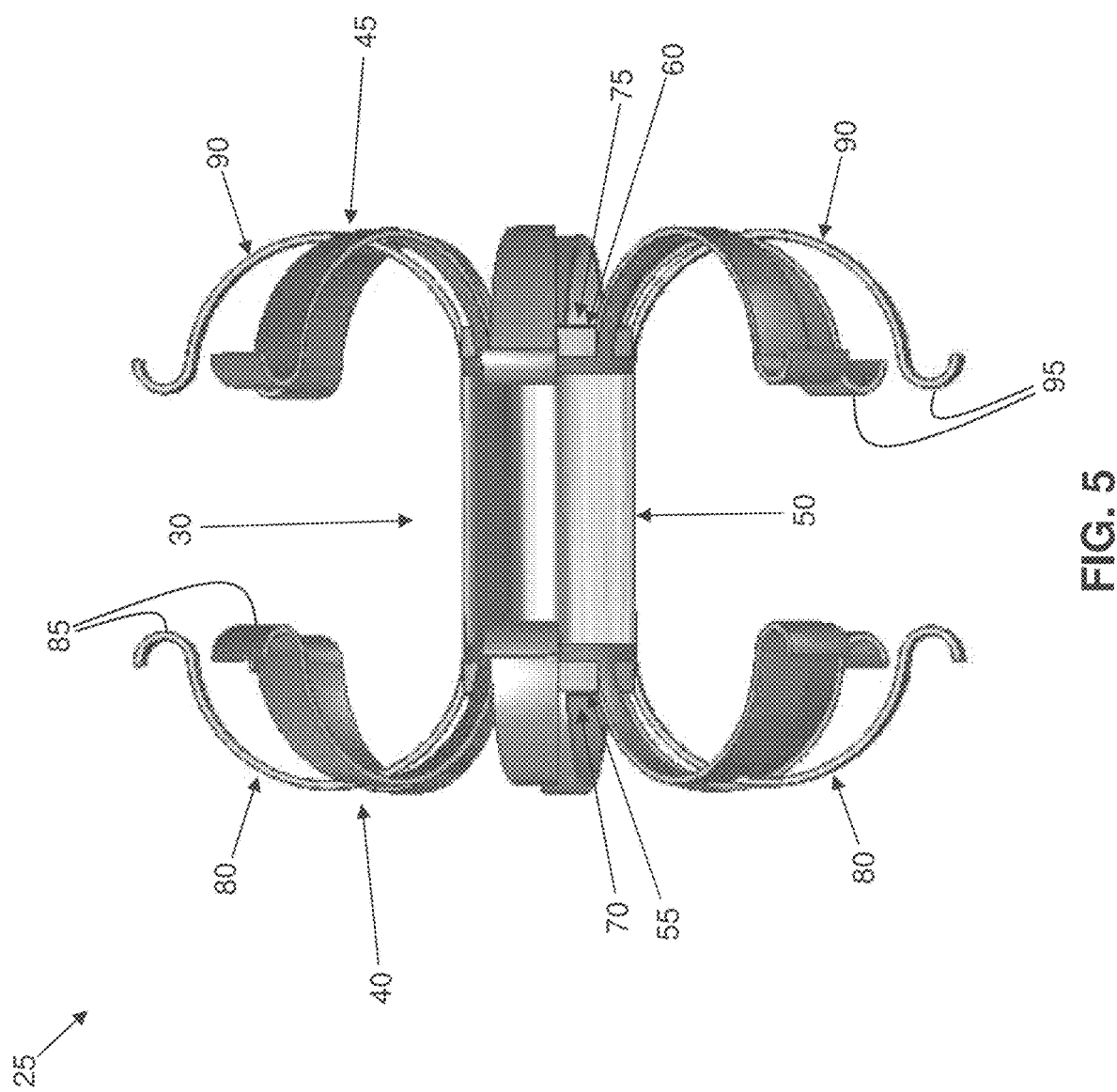
FIGS. 5-8 are schematic views showing a novel one-way valve formed in accordance with the present invention.
Figure 6:
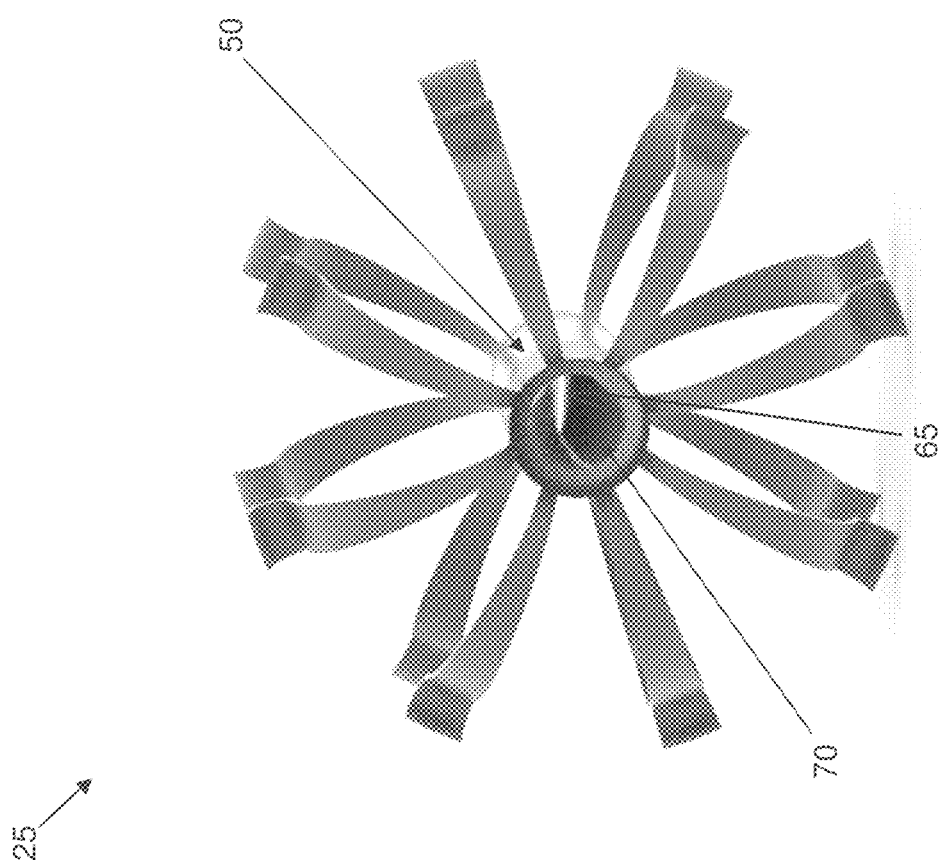
Figure 7:
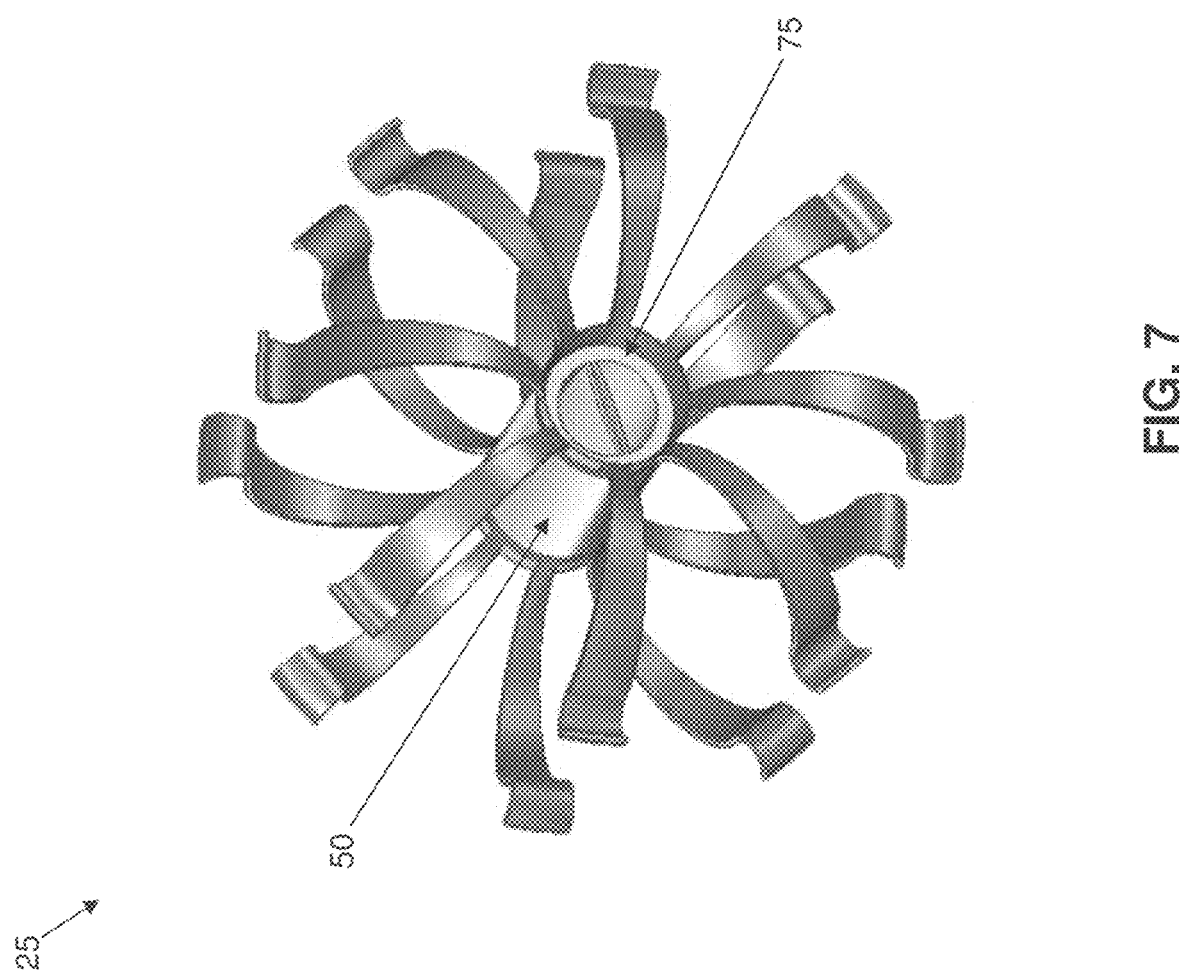
Figure 8:
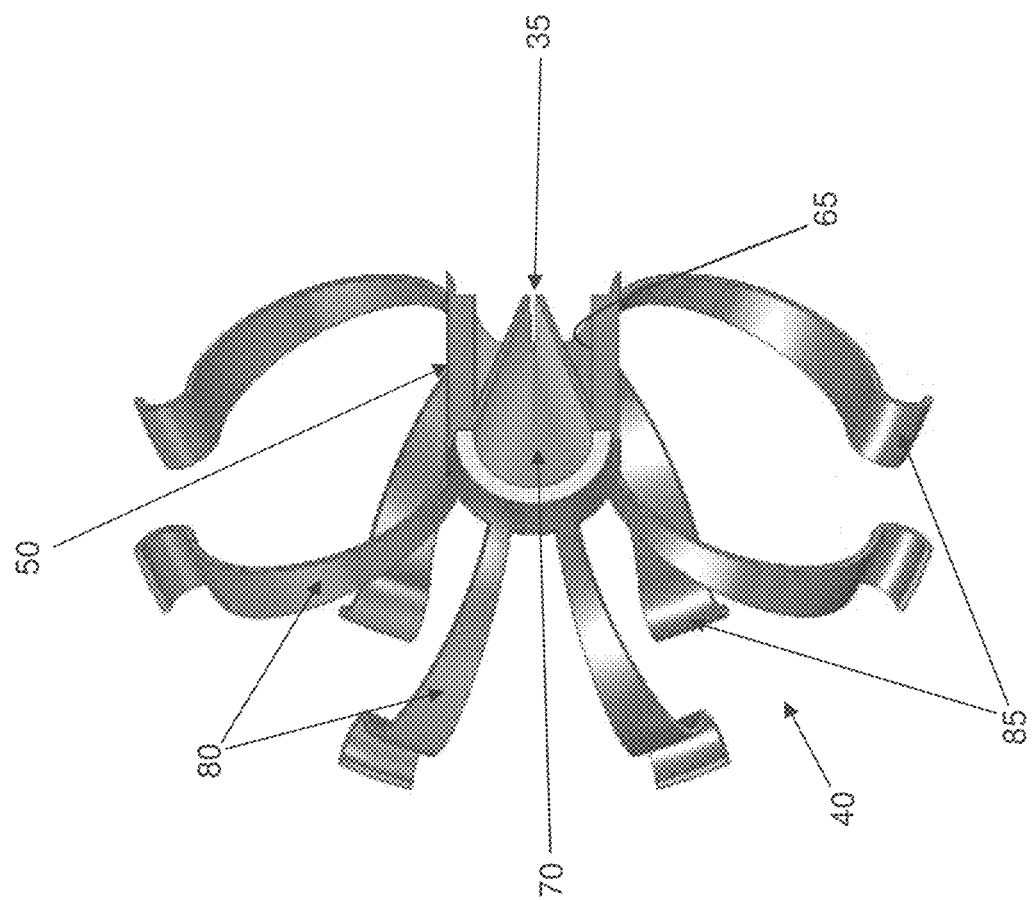

The present invention comprises the provision and use of a novel implantable one-way valve, and a novel method for treating a patient using the novel implantable one-way valve, so as to provide a direct connection between the abdominal cavity and the venous system of the patient.

For purposes of the present disclosure, the terms "proximal" and "distal" are used in the context of the fluid flow through the anatomy, i.e., the "proximal" direction is the direction towards the abdominal cavity containing the ascetic fluid and the "distal" direction is the direction towards the interior of the blood vessel which is to receive the ascetic fluid. Thus, for purposes of the present disclosure, the "proximal" end of the novel implantable one-way valve (see below) refers to the end of the novel implantable one-way valve directed toward the abdominal cavity containing the ascetic fluid and the "distal" end of the novel implantable one-way valve (see below) refers to the end of the novel implantable one-way valve directed toward the blood vessel which is to receive the ascetic fluid.

Novel One-Way Valve

In one preferred form of the invention, and looking now at FIGS. 5-8, there is shown a novel implantable one-way valve 25. One-way valve 25 generally comprises a body 30, a valve element 35, a proximal connection element 40 and a distal connection element 45.

More particularly, valve body 30 generally comprises a tube 50 having a proximal end 55, a distal end 60, and a lumen 65 extending therebetween. Lumen 65 comprises an inlet 70 disposed at proximal end 55 of tube 50 and an outlet 75 disposed at distal end 60 of tube 50.

In a preferred form of the present invention, tube 50 (and hence, lumen 65) comprises a generally circular cross-section and is radially compressible in order to aid in implantation of one-way valve 25 into a blood vessel, as will hereinafter be discussed in further detail. It should be appreciated that in a preferred form of the invention, the length of tube 50 can be selected such that the length of tube 50 is at least equal to the thickness of the wall of the blood vessel into which one-way valve 25 is to be implanted, plus the thickness of interstitial tissue (disposed between the wall of the blood vessel and the peritoneal layer) which tube 50 will need to extend through in order to reach the wall of the blood vessel, plus the thickness of the peritoneal layer which tube 50 will need to extend through. Furthermore, if desired, the diameter of tube 50 can be selected such that tube 50 will comprise a diameter smaller than the diameter of the blood vessel into which one-way valve 25 is to be implanted.

Valve element 35 is disposed within lumen 65 of tube 50, intermediate proximal end 55 of tube 50 and distal end 60 of tube 50. In one preferred form of the invention, valve element 35 comprises a one-way, slit-type valve such that fluid may enter into inlet 70, pass through the proximal portion of lumen 65, pass through valve element 35, pass through the distal portion of lumen 65 and exit out of outlet 75, but which does not allow fluid to flow in the opposite direction (i.e., from the blood vessel, through valve element 35 and into the abdominal cavity). As a result, when one-way valve 25 is implanted into a blood vessel (e.g., a vein) in the region of the abdominal cavity such that inlet 70 is open to ascetic fluid within the abdominal cavity and outlet 75 is open to the interior of the blood vessel, ascetic fluid can flow from the abdominal cavity, through one-way valve 25 and into the vein, but fluid cannot flow in the opposite direction.

It should be appreciated that valve element 35 is preferably configured such that valve element 35 is "closed" (i.e., does not permit fluid to flow) until the pressure differential between (i) the pressure of the fluid entering inlet 70, and (ii) the pressure of the fluid entering outlet 75, rises above a pre-determined threshold. By way of example but not limitation, valve element 35 may be configured to "open" (i.e., allow fluid to flow from inlet 70, through valve element 35 and out of outlet 75) when the pressure differential on the two sides of the valve element is less than 10 mmHg and, more preferably, when the pressure differential is between 2 mmHg and 5 mmHg.

Proximal connection element 40 is preferably mounted to proximal end 55 of tube 50 of valve body 30, and distal connection element 45 is preferably mounted to distal end 60 of tube 50 of valve body 30. Proximal connection element 40 and distal connection element 45 are preferably spaced apart from one another such that when one-way valve 25 is deployed at an internal site (e.g., across the wall of a blood vessel such as a vein, plus any interstitial tissue, plus the peritoneal layer), the blood vessel wall (plus interstitial tissue, plus the peritoneal layer) is captured between proximal connection element 40 and distal connection element 45, whereby to anchor one-way valve 25 in place within the wall of the blood vessel. To this end, the distance between proximal connection element 40 and distal connection element 45 is preferably equal to the thickness of the vessel wall to be spanned by one-way valve 25, plus any intervening tissue through which the deployed one-way valve 25 will pass (e.g., interstitial tissue, peritoneal layer, etc.).

Proximal connection element 40 preferably comprises a plurality of legs 80 extending radially outward from tube 50 and terminating in a plurality of distally-directed contact surfaces 85. Legs 80 are preferably spring-biased such that they can be radially constrained when one-way valve 25 is being delivered to an internal anatomical site (e.g., via a delivery sheath), and thereafter spring outward (e.g., when the delivery sheath is removed) such that legs 80 and/or distally-directed contact surfaces 85 engage the wall of the blood vessel (or the intervening tissue), whereby to anchor proximal connection element 40 (and hence, one-way valve 25) in position, as will hereinafter be discussed in further detail.

Distal connection element 45 preferably comprises a plurality of legs 90 extending radially outward from tube 50 and terminating in a plurality of proximally-directed contact surfaces 95. Legs 90 are preferably spring-biased such that they can be radially constrained when one-way valve 25 is being delivered to an internal anatomical site (e.g., via a delivery sheath), and thereafter spring outward (e.g., when the delivery sheath is removed) such that legs 90 and/or proximally-directed contact surfaces 95 engage the wall of the blood vessel (or the intervening tissue), whereby to anchor distal connection element 45 (and hence, one-way valve 25) in position, as will hereinafter be discussed in further detail.

In one preferred form of the invention, the distal end of one-way valve 25 (i.e., the portions of the one-way valve which extend into the interior of the blood vessel) are formed so as to be as smooth as possible so as to minimize thrombus formation.

Although one-way valve 25 is depicted in FIGS. 5-8 as having two connection elements (i.e., a proximal connection element 40 and a distal connection element 45), it should be appreciated that, if desired, one-way valve 25 may comprise only a single connection element. By way of example but not limitation, distal connection element 45 may be omitted. In this form of the invention, proximal connection element 40 is configured to anchor one-way valve 25 in the blood vessel (e.g., proximal connection element 40 might comprise a sewing ring for suturing proximal connection element 40 to the wall of the blood vessel or the intervening tissue). This may be advantageous in some applications, inasmuch as distal connection element 45 would otherwise be disposed within the interior of a blood vessel, and the omission of distal connection element 45 (i.e., legs 95 of distal connection element 45), which is typically disposed within the interior of the blood vessel, can minimize the incidence of thrombosis at the site of implantation.

Exemplary Use of One-Way Valve 25

Figure 9:
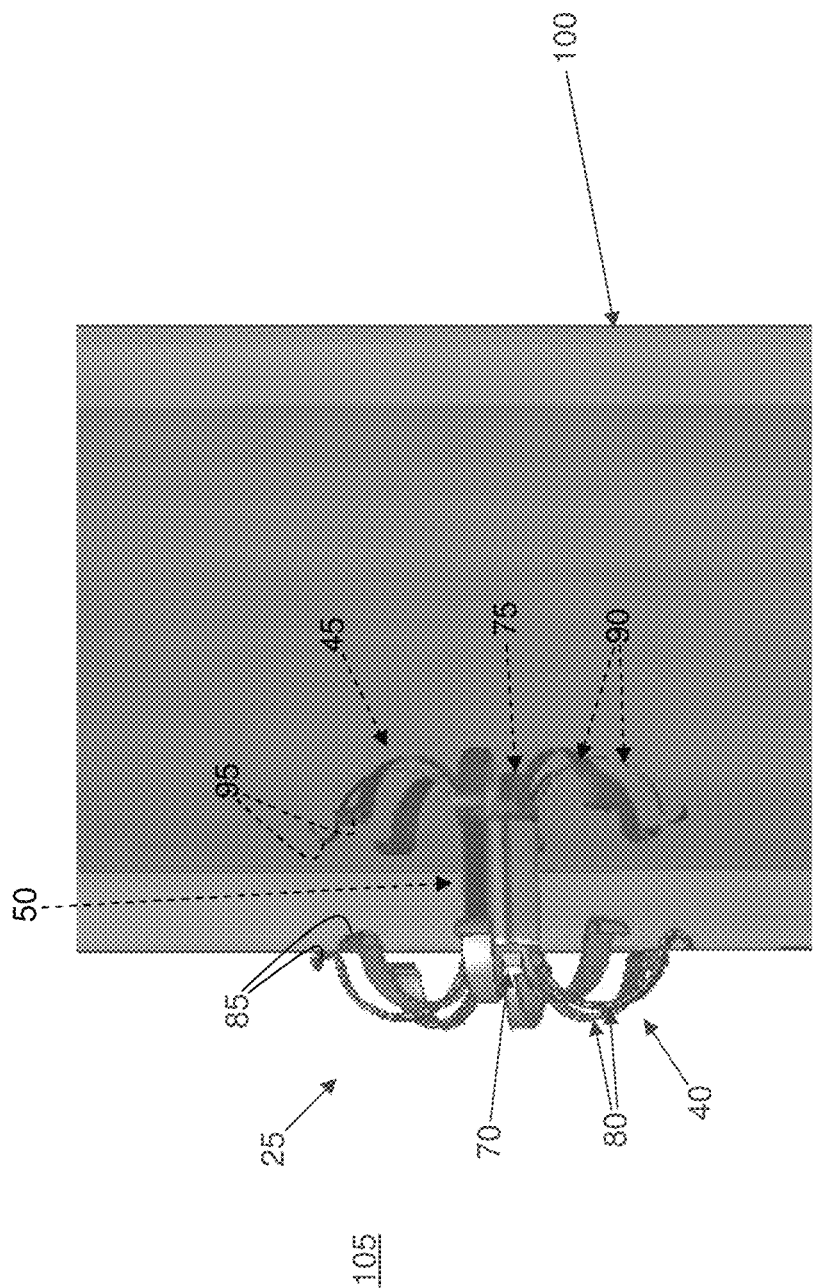
FIG. 9 is a schematic view showing the one-way valve of FIGS. 5-8 implanted in the side wall of a blood vessel.

In use, and looking now at FIG. 9, one-way valve 25 is preferably implanted into the peritoneum/interstitium (sometimes hereinafter referred to as the "peritoneal layer" and the "interstitial tissue" or "interstitial layer", respectively) and the wall of a blood vessel 100 (e.g., the vena cava, the vena iliaca, etc.) such that inlet 70 of one-way valve 25 is in fluid communication with the abdominal cavity 105 (e.g., such that inlet 70 is in fluid communication with the ascetic fluid), and outlet 75 is in fluid communication with the interior of blood vessel 100. Proximal connection element 40 contacts the outer wall of blood vessel 100 (or contacts the intervening tissue, e.g., the peritoneal layer and/or interstitial tissue), and distal connection element 45 contacts the inner wall of blood vessel 100, thereby anchoring one-way valve 25 within the wall of blood vessel 100 such that one-way valve 25 spans the blood vessel wall (and any intervening tissue) and provides a one-way fluid pathway from abdominal cavity 105, through tube 50 (and through valve element 35) into the interior of blood vessel 100.

As a result, fluid is able to flow from abdominal cavity 105, into inlet 70 of one-way valve 25, through valve element 35 and out of outlet 75 of one-way valve 25, into the interior of blood vessel 100.

As will hereinafter be discussed in further detail, a delivery system may be provided for implanting the one-way valve into the wall of the blood vessel.

As will also hereinafter be discussed in further detail, one-way valve 25 may be implanted using an "abdominal approach" in which the one-way valve is advanced from the abdominal cavity, through the wall of the blood vessel, and into the lumen of the blood vessel. Alternatively, one-way valve 25 may be implanted using an "endoluminal approach" in which the one-way valve is advanced from the lumen of the blood vessel, through the wall of the blood vessel, and into the abdominal cavity.

Delivery System for Delivering and Deploying One-Way Valve 25

As discussed above, one-way valve 25 is configured to be implanted into the side wall of a blood vessel (e.g., a vein) at an internal anatomical site in order to facilitate treatment of ascites. To this end, it is desirable to provide a novel delivery system for delivering one-way valve 25 to an internal anatomical site, and for deploying one-way valve 25 into the side wall of the blood vessel.

Looking next at FIG. 10, there is shown a novel delivery system 110. Delivery system 110 generally comprises a puncture device 115, a guidewire 120, a deployment catheter 125 and a delivery sheath 130. Also shown in FIG. 10 is one-way valve 25 loaded on guidewire 120 and disposed within deployment catheter 125.

More particularly, puncture device 115 preferably comprises an elongated shaft having a sharp distal end which may be used to penetrate through tissue (e.g., through the peritoneal layer, through interstitial tissue, through the wall of a blood vessel, etc.).

Guidewire 120 comprises a flexible guidewire of the sort well known in the art which may be used to guide one-way valve 25 to an internal site, as will hereinafter be discussed in further detail.

Deployment catheter 125 generally comprises a tube having an open distal end, an open proximal end, and a lumen extending therebetween. The lumen of deployment catheter 125 is sized so as to hold one-way valve 25 in a radially-contracted condition, e.g., with legs 80 of proximal connection element 40 and legs 90 of distal connection element 45 being held parallel to valve body 30, whereby to provide a reduced profile for delivery of one-way valve 25 to an internal anatomical site, as will hereinafter be discussed in further detail.

Delivery sheath 130 generally comprises a tube having an open distal end, an open proximal end, and a lumen extending therebetween. Delivery sheath 130 is sized so as to fit over deployment catheter 125, whereby to protect deployment catheter 125 and one-way valve 25 during delivery to an internal anatomical site, as will hereinafter be discussed in further detail.

Method of Implanting and Deploying One-Way Valve 25

As discussed above, one-way valve 25 is intended to be deployed in the side wall of a blood vessel proximate to the abdominal cavity such that fluid can flow from the abdominal cavity, through one-way valve 25, and into the interior of the blood vessel. One-way valve 25 may be deployed at an internal anatomical site using various methods (e.g., open surgery, percutaneous deployment, endoluminal deployment, etc.) or combinations thereof.

By way of example but not limitation, and looking now at FIGS. 11-13, one-way valve 25 may be implanted using an "abdominal approach" in which the one-way valve is advanced from the abdominal cavity, through the wall of the blood vessel, and into the lumen of the blood vessel.

By way of example but not limitation, in order to prepare the internal site for implantation of one-way valve 25, the surgeon first extracts the ascetic fluid from the abdominal cavity (e.g., using a syringe, a collection bag, suction, etc.). The abdominal cavity is then rinsed (e.g., with saline) and drained (e.g., using a syringe, collection bag, suction, etc.). If desired, one or more access ports (e.g., access cannulas) may be inserted into the patient's abdomen (i.e., through the skin) in order to provide the surgeon with access to the abdominal cavity and to visualize/access the blood vessel into which one-way valve 25 is to be implanted. By way of example but not limitation, the surgeon may use the access ports to insert optical devices, instruments, etc. into the abdominal cavity in order to help the surgeon locate the blood vessel (e.g., the inferior vena cava, the common iliac veins, etc.) into which one-way valve 25 is to be implanted.

Puncture device 115 of delivery system 110 may be advanced from the abdominal cavity (e.g., through delivery sheath 130) so that it passes through the side wall of the blood vessel so as to form a hole in the side wall of the blood vessel, and then deployment catheter 125 (passing through delivery sheath 130) may be used to bring one-way valve 25 (with its proximal connection element 40 and its distal connection element 45 in their radially contracted conditions) through the hole formed in the side wall of the blood vessel. Then deployment catheter 125 is removed so that proximal connection element 40 and distal connection element 45 assume their radially expanded conditions, whereby to secure one-way valve 25 in the side wall of the blood vessel. Delivery sheath 130 may then be removed. At the conclusion of the procedure, one-way valve 25 is securely anchored within the side wall of the blood vessel (e.g., the inferior vena cava), held in position by proximal connection element 40 and distal connection element 45. Inlet 70 of tube 50 of one-way valve 25 is fluidically connected to the abdominal cavity and outlet 75 of tube 50 of one-way valve 25 is fluidically connected to the blood vessel (e.g., the interior of the inferior vena cava). As a result, fluid (e.g., fluid resulting from ascites) is able to flow from the abdominal cavity, into inlet 70 of tube 50, along lumen 65 of tube 50, through valve element 35 and out outlet 75 of tube 50 into the interior of the blood vessel (e.g., the interior of the inferior vena cava), but fluid is unable to flow in the opposite direction. Thus, fluid can exit the abdominal cavity and enter the blood vessel without the need for a long catheter or the need for external access to the abdominal cavity.

Figure 15:
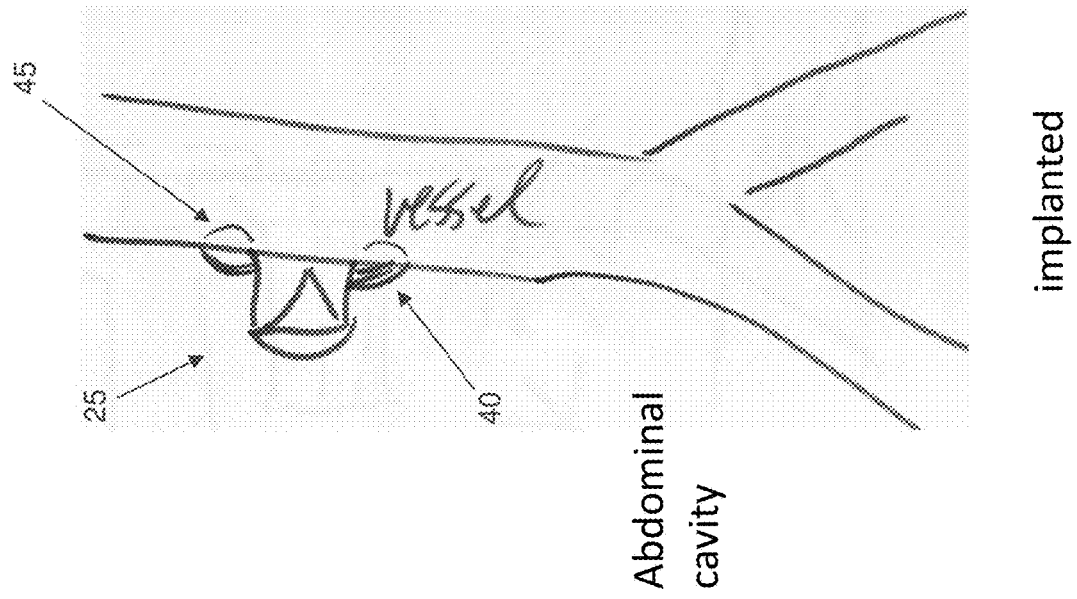
FIGS. 14, 15, 15A and 15B are schematic views showing how a novel one-way valve formed in accordance with the present invention may be implanted into the side wall of a blood vessel using an "endoluminal approach"
Figure 14:
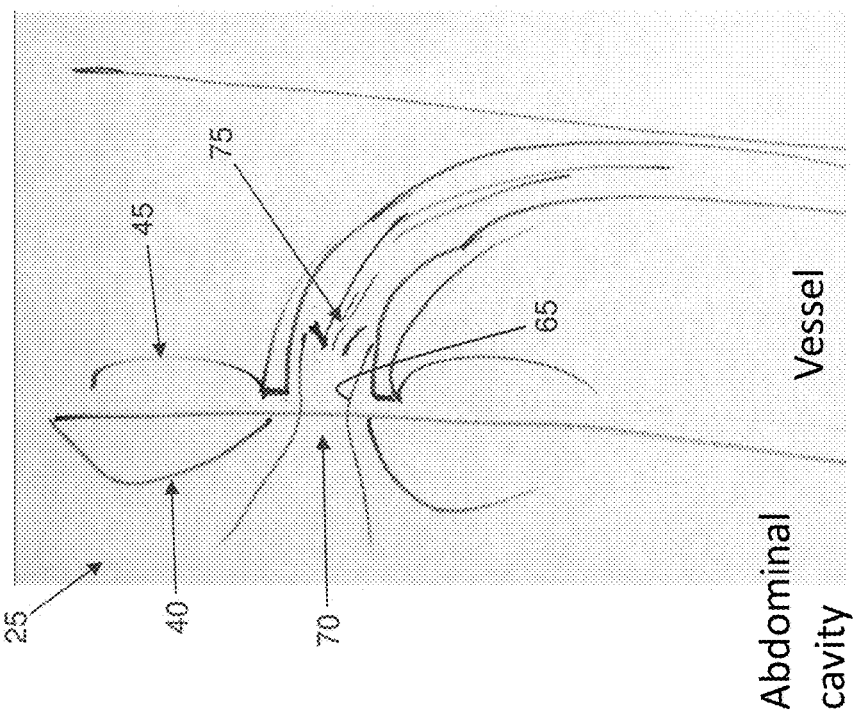

Alternatively, and looking now at FIGS. 14 and 15, one-way valve 25 may be implanted using an "endoluminal approach". In a preferred form of the present invention, one-way valve 25 is implanted using an endovascular approach in which the one-way valve is advanced from the lumen of the blood vessel, through the wall of the blood vessel, and into the abdominal cavity.

By way of example but not limitation, in order to prepare the internal site for implantation of one-way valve 25, the surgeon first extracts the ascetic fluid from the abdominal cavity (e.g., using a syringe, a collection bag, suction, etc.). If desired, fluid may also be drained from the abdominal cavity using novel delivery system 110 (e.g., by draining the abdominal cavity using deployment catheter 125 and/or delivery sheath 130). The abdominal cavity is then rinsed (e.g., with saline) and drained (e.g., using a syringe, collection bag, suction, etc.). If desired, one or more access ports (e.g., access cannulas) may be inserted into the patient's abdomen (i.e., through the skin) in order to provide the surgeon with access to the abdominal cavity and to visualize/access the blood vessel into which one-way valve 25 is to be implanted, however, it should be appreciated that such access ports in the patient's abdomen are generally unnecessary when using an endovascular approach to implant one-way valve 25. By way of example but not limitation, the surgeon may use the access ports to insert optical devices, instruments, etc. into the abdominal cavity in order to help the surgeon locate the blood vessel (e.g., the inferior vena cava, the common iliac veins, etc.) into which one-way valve 25 is to be implanted.

Figure 15A:
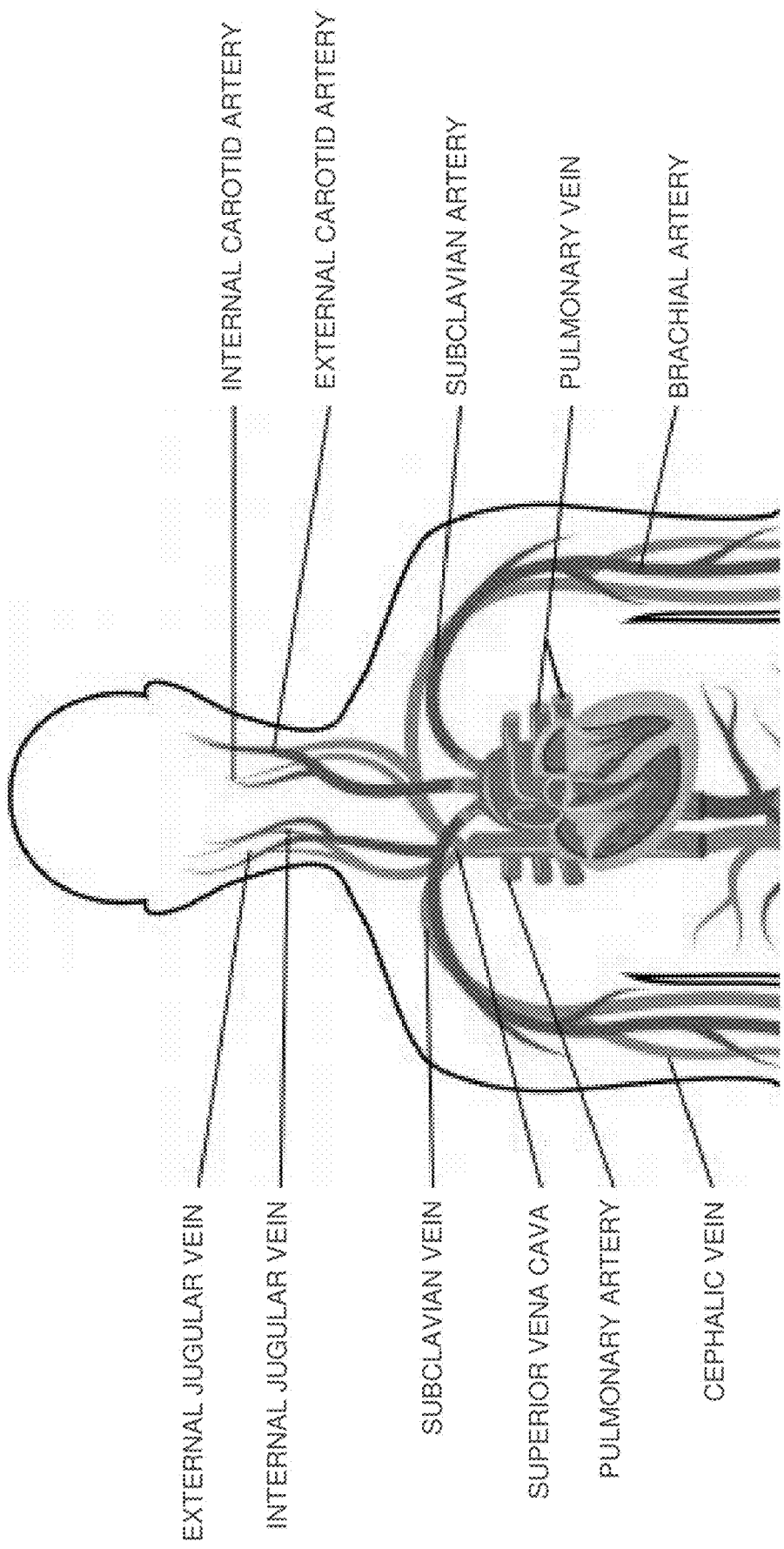
Figure 15B:
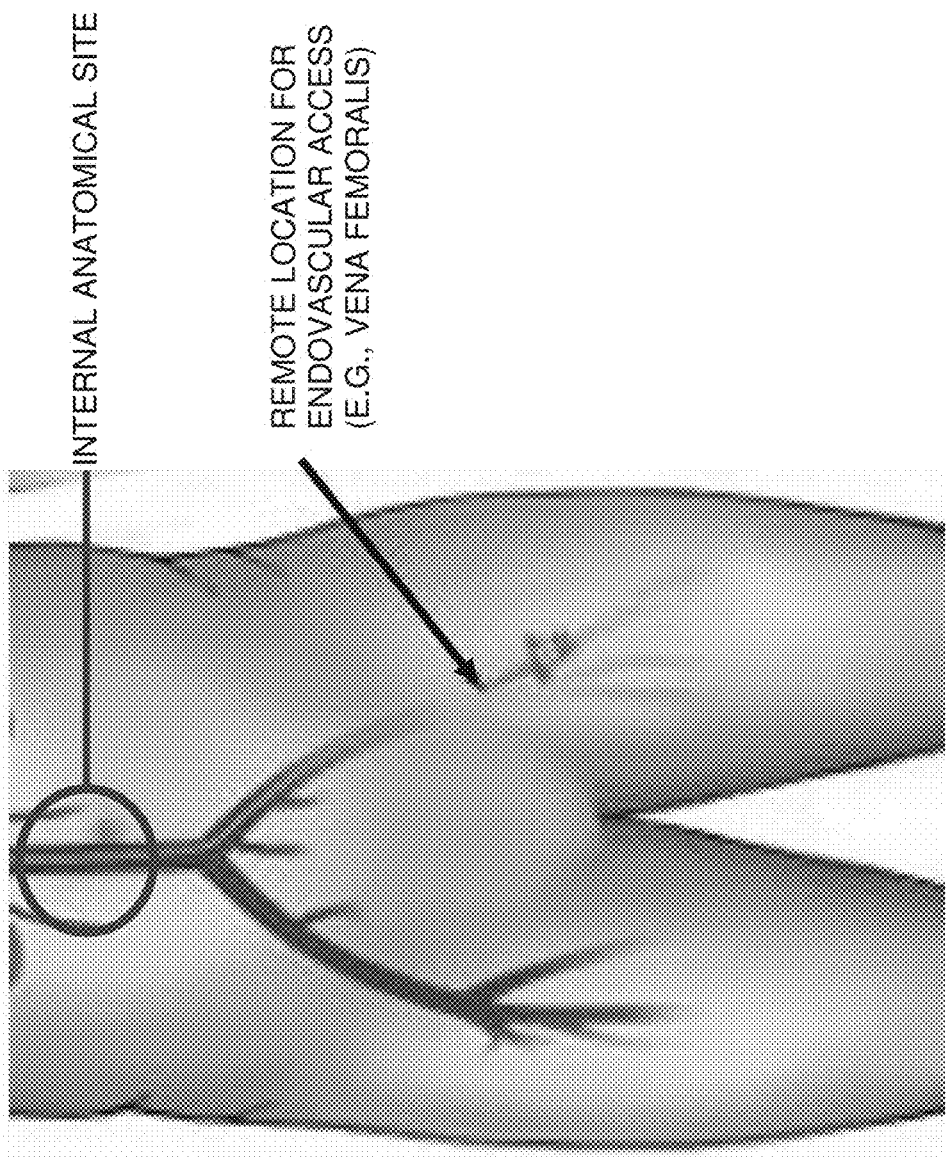
Figure 18:
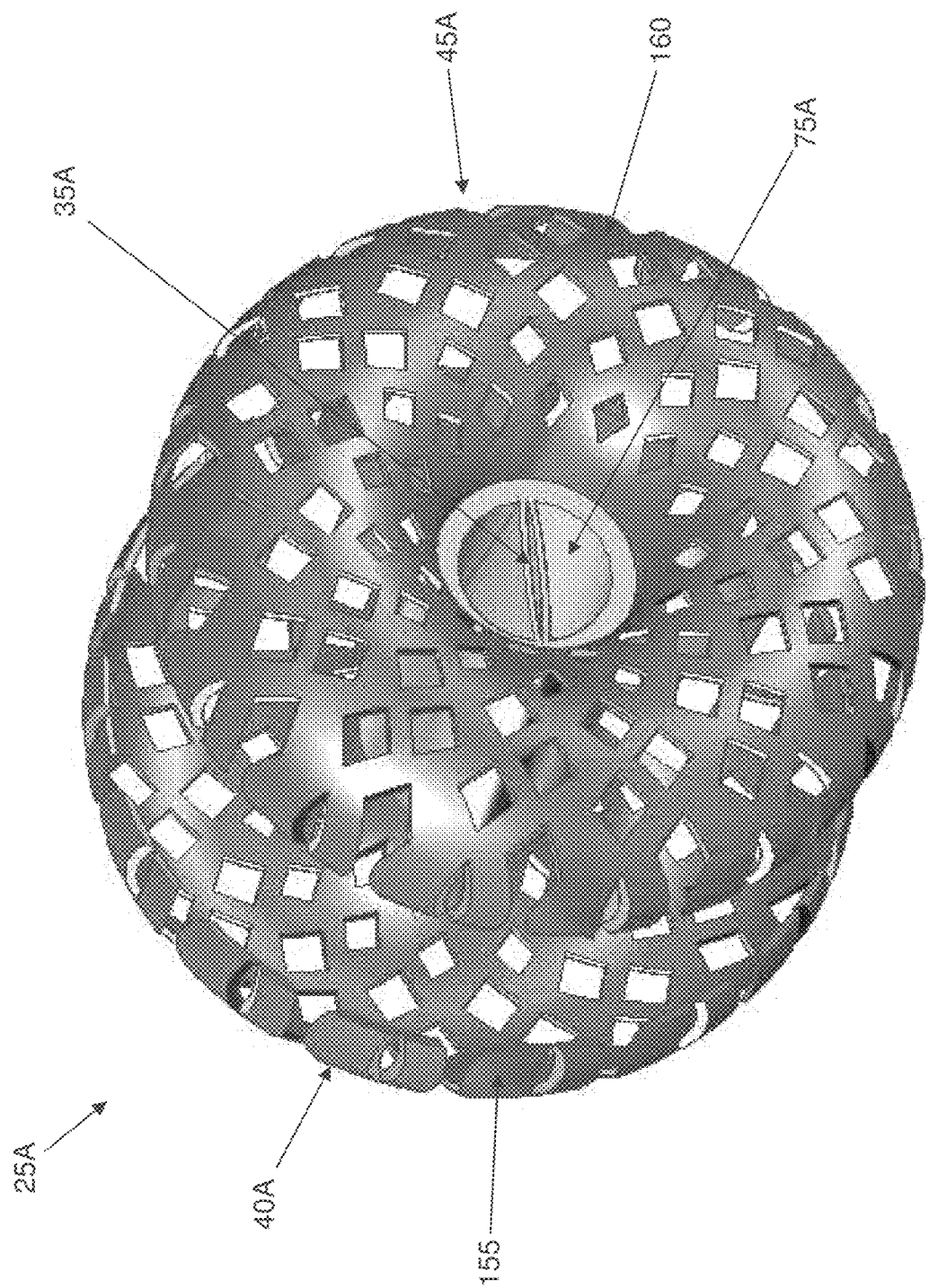
Figure 19:
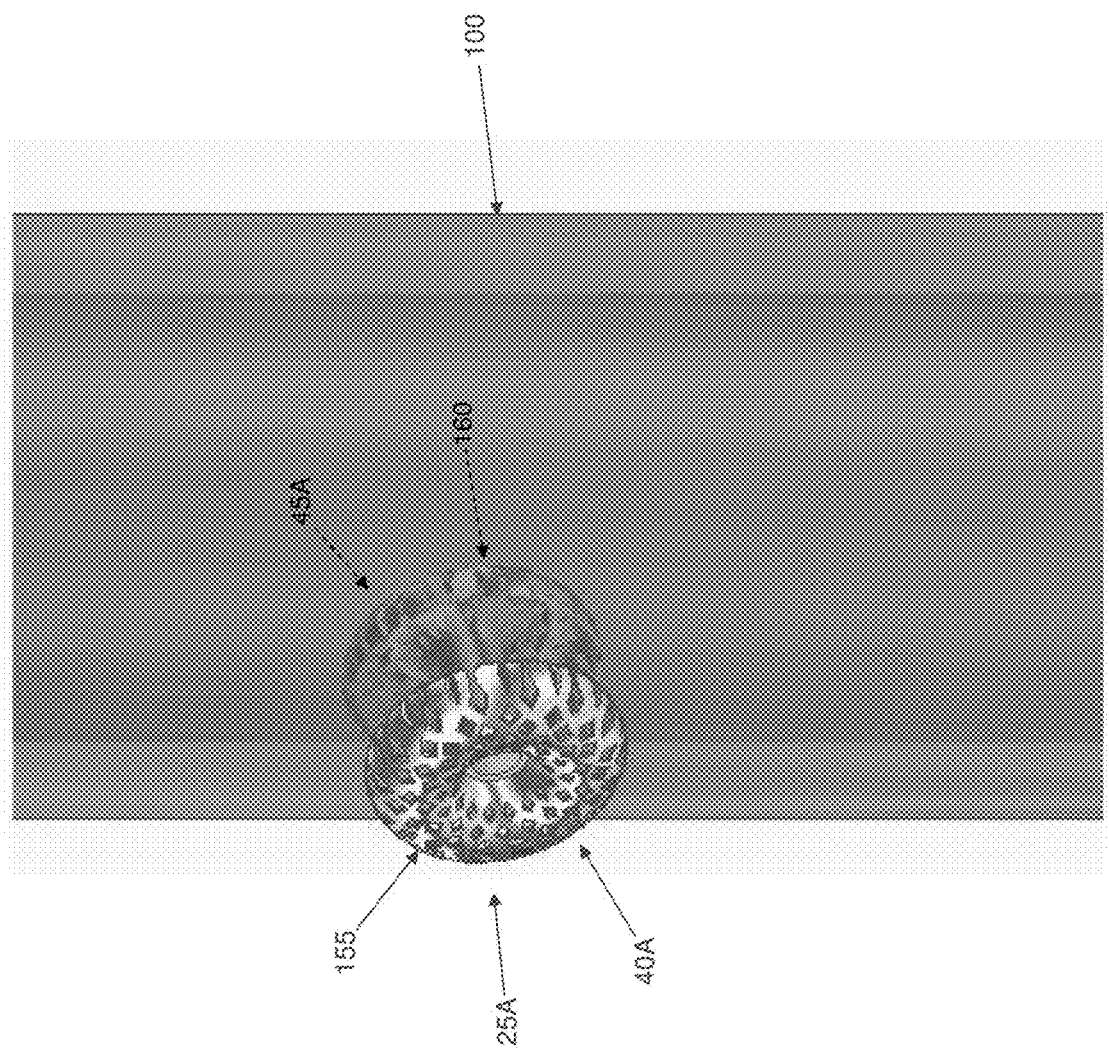
FIG. 19 is a schematic view showing the one-way valve of FIGS. 16-18 implanted in the side wall of a blood vessel.

After the surgeon has located a suitable blood vessel for implantation and identified a suitable implantation site (i.e., a suitable blood vessel for receiving one-way valve 25 proximate to the abdominal cavity), puncture device 115 is used to puncture the skin of the patient so as to access the interior of a blood vessel. In a preferred form of the invention, access to the vasculature is made by puncturing the jugular vein (FIG. 15A) using a puncture device 115 and then the one-way valve is advanced to the selected internal site endoluminally. Alternatively, access to the vasculature may be achieved by puncturing the subclavian vein (also known as the vena subclavia) and then one-way valve is advanced to the internal site endoluminally. In still another form of the invention, access to the vasculature is made via the vena femoralis (FIG. 15B) at a location remote from the patient's abdomen (e.g., the thigh, groin, etc.) in order to allow endoluminal advancement of one-way valve 25 to the selected internal anatomical site. Guidewire 120 is then inserted into the blood vessel (e.g., the jugular vein) and advanced through the puncture site endoluminally until the guidewire is disposed at the internal anatomical site (e.g., the desired location within the inferior vena cava).

Delivery sheath 130 is then advanced to the internal anatomical site by passing delivery sheath 130 over guidewire 120.

Puncture device 115 is then advanced to the internal anatomical site and used to puncture the side wall of the blood vessel (e.g., the distal inferior vena cava, distal to the inflow of the renal veins so as to avoid damaging the duodenum) at the internal anatomical site where one-way valve 25 is to be implanted, and to puncture any intervening tissue, whereby to create a path between the interior of the blood vessel and the abdominal cavity.

Deployment catheter 125, carrying one-way valve 25 within the lumen of deployment catheter 125, is then advanced to the internal anatomical site through the lumen of delivery sheath 130, and deployment catheter 125 is advanced through the puncture site in the side wall of the blood vessel (e.g., the inferior vena cava) and into the abdominal cavity. It should be appreciated that at this time, one-way valve 25 is disposed just inside the distal end of deployment catheter 125 (or, alternatively, one-way valve 25 may be advanced to a position just inside the distal end of deployment catheter 125). When one-way valve 25 is disposed in the desired position, the surgeon deploys one-way valve either by (i) pushing one-way valve 25 such that proximal connection element 40 is advanced out of the lumen of deployment catheter 125, or (ii) by withdrawing deployment catheter 125 such that proximal connection element 40 is freed from the lumen of deployment catheter 125, or (iii) by a combination of the foregoing techniques. As the radially-constricted legs 80 of proximal connection element 40 are released from deployment catheter 125, legs 80 expand radially outward, with distally-directed contact surfaces 85 contacting the outer wall of the blood vessel (or the interstitial tissue covering the outer wall of the blood vessel).

Next, deployment catheter 125 is withdrawn further until distal connection element 45, which is disposed within the interior of the blood vessel (e.g., the interior of the inferior vena cava), is uncovered. As the radially-constricted legs 90 of distal connection element 45 are released from deployment catheter 125, legs 90 expand radially outward into their radially-expanded configuration, with proximally-directed contact surfaces 95 contacting the inner wall of the blood vessel. At this point, one-way valve 25 is locked in position within the side wall of the blood vessel.

Finally, deployment catheter 125 is withdrawn so as to remove the deployment catheter from the patient's body, and then guidewire 120 and delivery sheath 130 are also withdrawn from the patient's body.

At the conclusion of the procedure, one-way valve 25 is securely anchored within the side wall of the blood vessel (e.g., the inferior vena cava), held in position by proximal connection element 40 and distal connection element 45. Inlet 70 of tube 50 of one-way valve 25 is fluidically connected to the abdominal cavity and outlet 75 of tube 50 of one-way valve 25 is fluidically connected to the blood vessel (e.g., the interior of the inferior vena cava). As a result, fluid (e.g., fluid resulting from ascites) is able to flow from the abdominal cavity, into inlet 70 of tube 50, along lumen 65 of tube 50, through valve element 35 and out outlet 75 of tube 50 into the interior of the blood vessel (e.g., the interior of the inferior vena cava), but fluid is unable to flow in the opposite direction. Thus, fluid can exit the abdominal cavity and enter the blood vessel without the need for a long catheter or the need for external access to the abdominal cavity.

Alternative One-Way Valve

Looking now at FIGS. 16-19, there is shown another one-way valve 25A formed in accordance with the present invention. One-way valve 25A is substantially identical to the one-way valve 25 discussed above, however, proximal connection element 40 and distal connection element 45 are replaced by proximal connection element 40A and distal connection element 45A, respectively.

More particularly, one-way valve 25A generally comprises a body 30A, a valve element 35A, a proximal connection element 40A and a distal connection element 45A.

Body 30A generally comprises a tube 50A having a proximal end 55A, a distal end 60A, and a lumen 65A extending therebetween. Lumen 65A comprises an inlet 70A disposed at proximal end 55A of tube 50A and an outlet 75A disposed at distal end 60A of tube 50A.

In one form of the present invention, tube 50A (and hence, lumen 65A) comprises a generally circular cross-section and is radially compressible in order to aid in implantation of one-way valve 25A into a blood vessel, as will hereinafter be discussed in further detail. It should be appreciated that in a preferred form of the invention, the length of tube 50A can be selected such that the length of tube 50A is at least equal to the thickness of the wall of the blood vessel into which one-way valve 25A is to be implanted, plus the thickness of interstitial tissue which tube 50A will need to extend through in order to reach the wall of the blood vessel, plus the thickness of the peritoneal layer which tube 50A will need to extend through. Furthermore, if desired, the diameter of tube 50A can be selected such that tube 50A will comprise a diameter smaller than the diameter of the blood vessel into which one-way valve 25A is to be implanted.

Valve element 35A is disposed within lumen 65A of tube 50A, intermediate proximal end 55A and distal end 60A of tube 50A. In one form of the invention, valve element 35A comprises a one-way slit-type valve which allows fluid to enter into inlet 70A, pass through the proximal portion of lumen 65A, pass through valve element 35A, pass through the distal portion of lumen 65A and exit lumen 65A out of outlet 75A, but which does not allow fluid to flow in the opposite direction (i.e., from the blood vessel, through valve element 35A and into the abdominal cavity). As a result, when one-way valve 25A is implanted into a blood vessel (e.g., a vein) in the region of the abdominal cavity such that inlet 70A is open to fluid within the abdominal cavity and outlet 75A is open to the interior of a blood vessel, fluid can flow from the abdominal cavity, through one-way valve 25A and into the blood vessel, but fluid cannot flow in the opposite direction.

It should be appreciated that valve element 35A is preferably configured such that valve element 35A is "closed" (i.e., does not permit fluid to flow) until the pressure differential between (i) the pressure of the fluid entering inlet 70A, and (ii) the pressure of the fluid entering outlet 75A, rises above a pre-determined threshold. By way of example but not limitation, valve element 35A may be configured to "open" (i.e., allow fluid to flow from inlet 70A, through valve element 35A and out of outlet 75A) when the pressure differential on the two sides of the valve element is less than 10 mmHg and, more preferably, when the pressure differential is between 2 mmHg and 5 mmHg.

Proximal connection element 40A is preferably mounted to proximal end 55A of tube 50A of valve body 30A, and distal connection element 45A is preferably mounted to distal end 60A of tube 50A of valve body 30A. Proximal connection element 40A and distal connection element 45A are preferably spaced apart from one another such that when one-way valve 25A is deployed at an internal site (e.g., across the wall of a blood vessel such as a vein), the blood vessel wall is captured between proximal connection element 40A and distal connection element 45A, whereby to anchor one-way valve 25A in place within the wall of the blood vessel. To this end, the distance between proximal connection element 40A and distal connection element 45A is preferably equal to the thickness of the vessel wall to be spanned by one-way valve 25A plus any intervening tissue through which the deployed one-way valve 25A will pass (e.g., interstitial tissue, peritoneal layer, etc.).

Proximal connection element 40A is similar to the aforementioned proximal connection element 40, however, proximal connection element 40A comprises a radially expandable mesh basket 155, rather than a plurality of legs 80, for engaging the outer wall of the blood vessel. More particularly, basket 155 of proximal connection element 40A is preferably spring-biased such that basket 155 will automatically deploy radially outward when proximal connection element 40A is unconstrained (i.e., released from deployment catheter 125 in the manner discussed above).

Distal connection element 45A is similar to the aforementioned distal connection element 45, however, distal connection element 45A comprises a radially expandable mesh basket 160, rather than a plurality of legs 80, for engaging the inner wall of the blood vessel. More particularly, basket 160 of distal connection element 45A is preferably spring-biased such that basket 160 will automatically deploy radially outward when distal connection element 45A is unconstrained (i.e., released from deployment catheter 125 in the manner discussed above).

Although one-way valve 25A is depicted in FIGS. 16-19 as having two connection elements (i.e., a proximal connection element 40A and a distal connection element 45A), it should be appreciated that, if desired, one-way valve 25A may comprise only a single connection element. By way of example but not limitation, distal connection element 45A may be omitted. In this form of the invention, proximal connection element 40A is configured to anchor one-way valve 25A in the blood vessel (e.g., proximal connection element 40A might comprise a sewing ring for suturing proximal connection element 40A to the wall of the blood vessel or the intervening tissue). This may be advantageous in some applications, inasmuch as distal connection element 45A would otherwise be disposed within the interior of a blood vessel, and the omission of distal connection element 45A (i.e., radially expandable mesh basket 160 of distal connection element 45A), which is typically disposed within the interior of the blood vessel, can minimize the incidence of thrombosis at the site of implantation.

Alternative Valve Elements

In the foregoing descriptions, valve elements 35/35A are shown and described as slit-type valves which automatically open in order to allow fluid flow in a single, pre-determined direction (i.e., from the abdominal cavity, through valve element 35/35A and out to the interior of the blood vessel) when the pressure differential across the valve element exceeds a pre-determined threshold.

However, it should be appreciated that valve elements 35/35A may be provided in various other configurations if desired.

Figure 20:
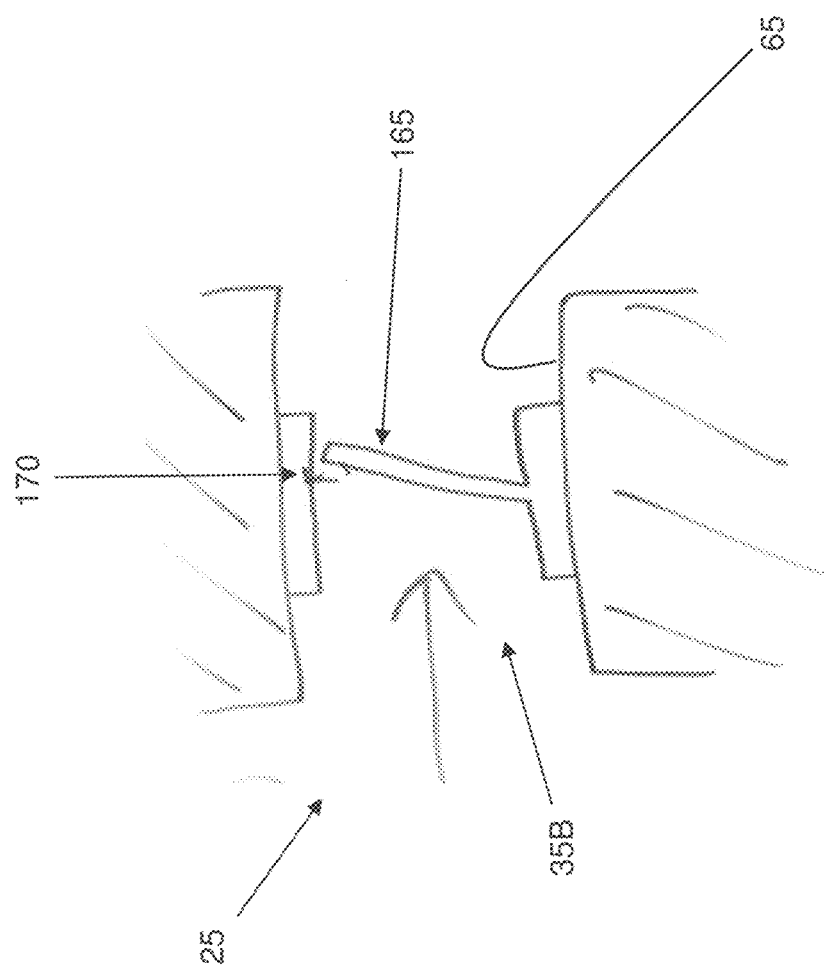
FIGS. 20-24 are schematic views which show alternative valve elements which may be used with the novel one-way valve of the present invention.

By way of example but not limitation, and looking now at FIG. 20, there is shown a valve element 35B which comprises a flexible flap 165 which pivots away from a stop 170 when the pressure differential across the valve exceeds a predetermined threshold, whereby to allow fluid flow, but which seats against stop 170 when the pressure differential across the valve falls below a predetermined threshold. In this way, valve element 35B provides one-way flow through lumen 65 of one-way valve 25.

Figure 21:
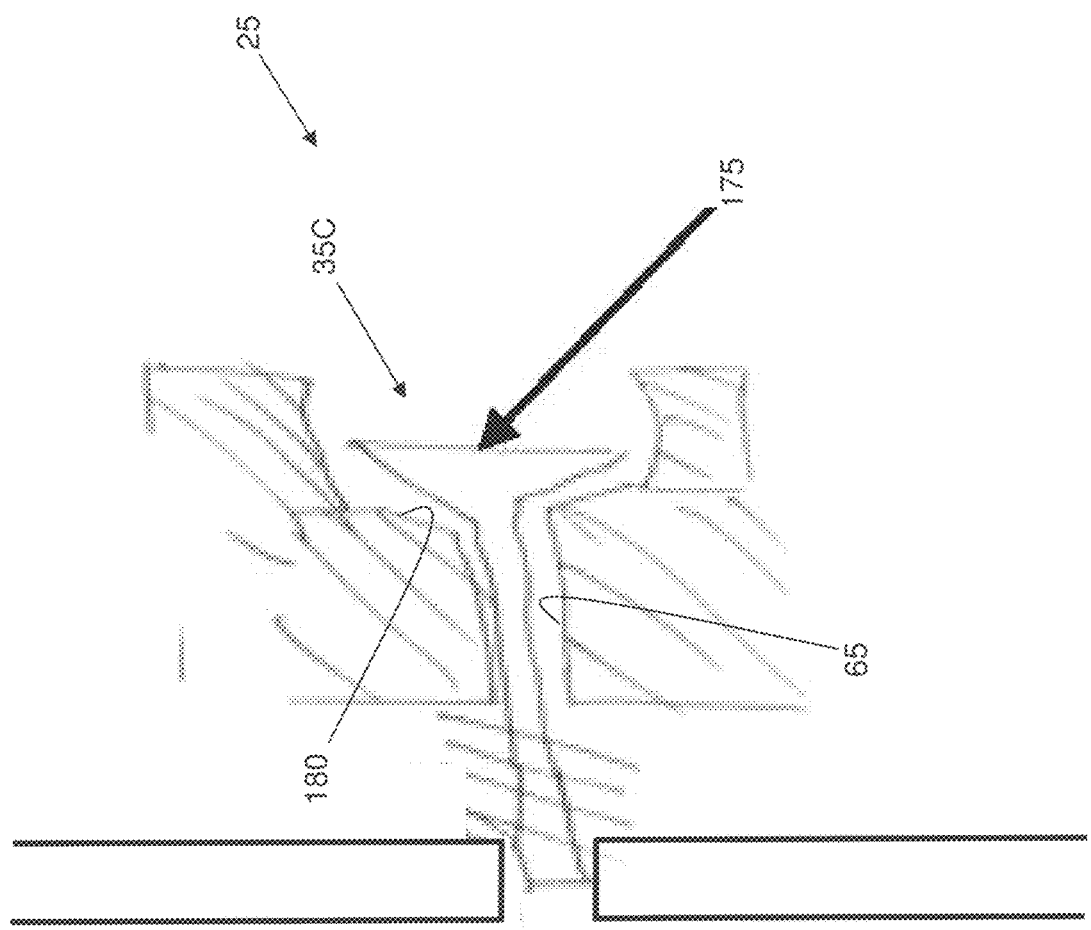

By way of further example but not limitation, and looking now at FIG. 21, there is shown a valve element 35C which comprises a spring-biased plunger 175 which is configured to move longitudinally away from a stop 180 when the pressure differential across the valve exceeds a predetermined threshold, whereby to allow fluid flow, but which seats against stop 180 when the pressure differential across the valve falls below a predetermined threshold. In this way, valve element 35C provides one-way flow through lumen 65 of one-way valve 25.

Figure 22:
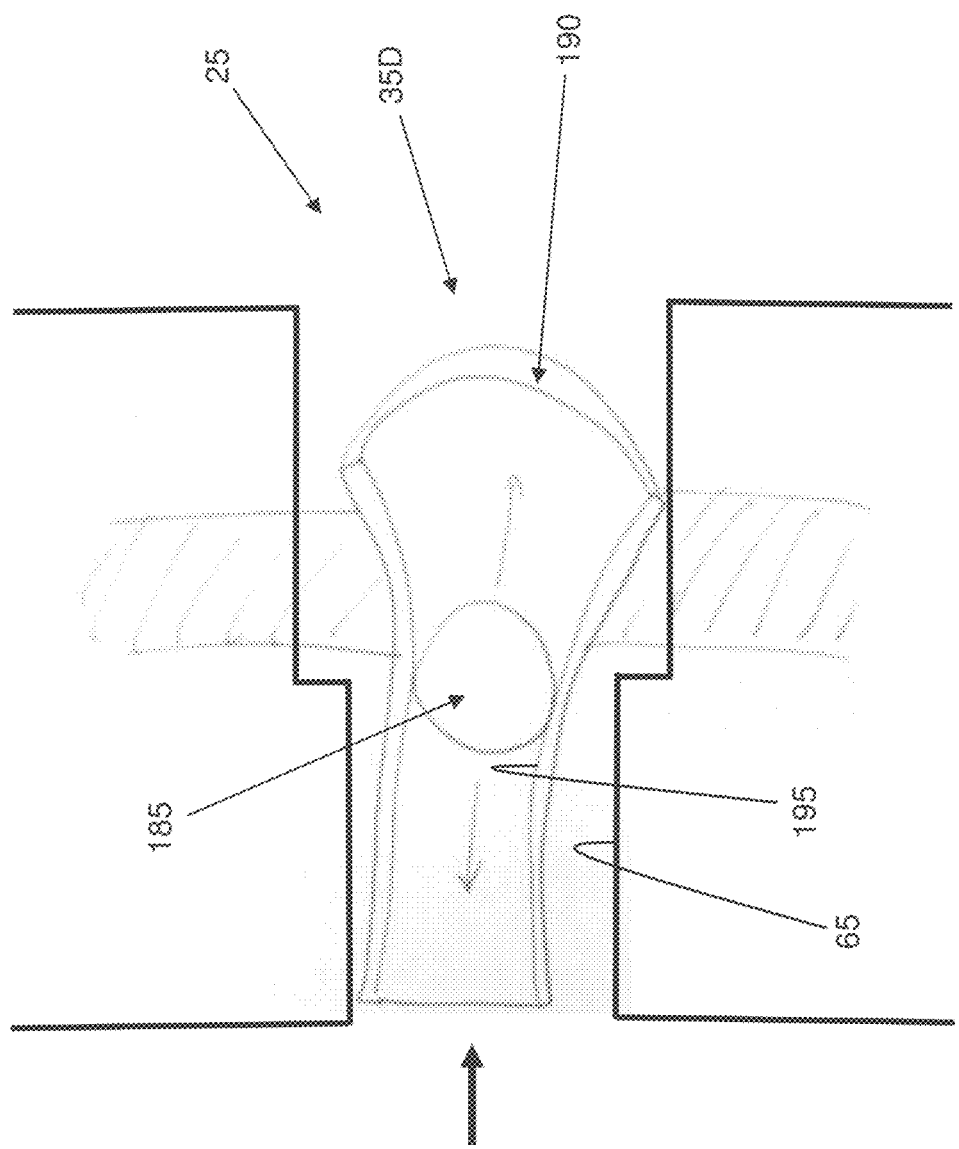

By way of further example but not limitation, and looking now at FIG. 22, there is shown a valve element 35D which comprises a ball 185 which is configured to move longitudinally within a cage 190, so that ball 185 can move away from a stop 195 when the pressure differential across the valve exceeds a predetermined threshold, whereby to allow fluid flow, but which seats against stop 195 when the pressure differential across the valve falls below a predetermined threshold. In this way, valve element 35D provides one-way flow through lumen 65 of one-way valve 25.

Figure 23:
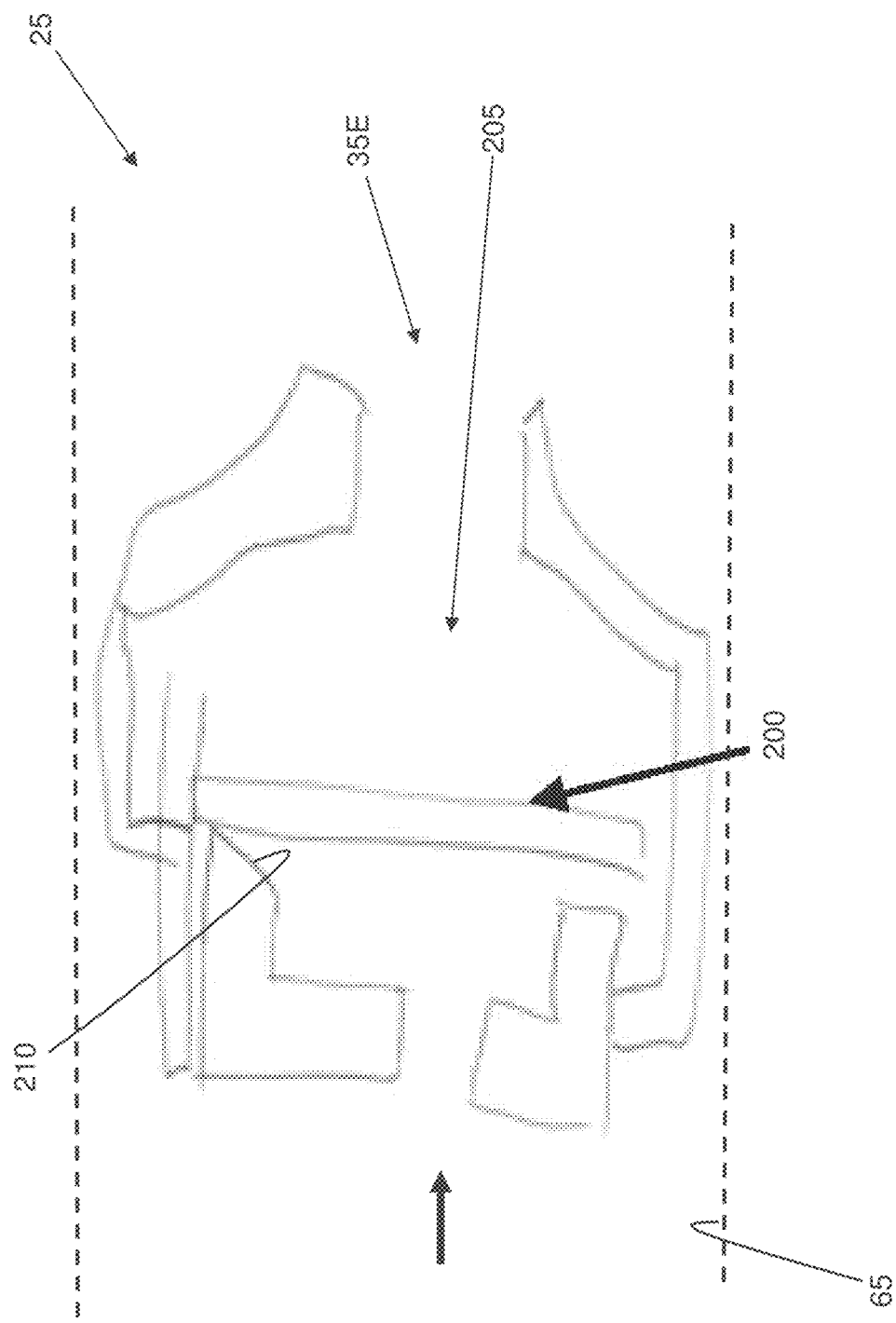

By way of further example but not limitation, and looking now at FIG. 23, there is shown a valve element 35E which comprises a disc 200 which is configured to move longitudinally within a chamber 205, so that disc 200 can move away from a stop 210 when the pressure differential across the valve exceeds a predetermined threshold, whereby to allow fluid flow, but which seats against stop 210 when the pressure differential across the valve falls below a predetermined threshold. In this way, valve element 35E provides one-way flow through lumen 65 of one-way valve 25.

Figure 24:
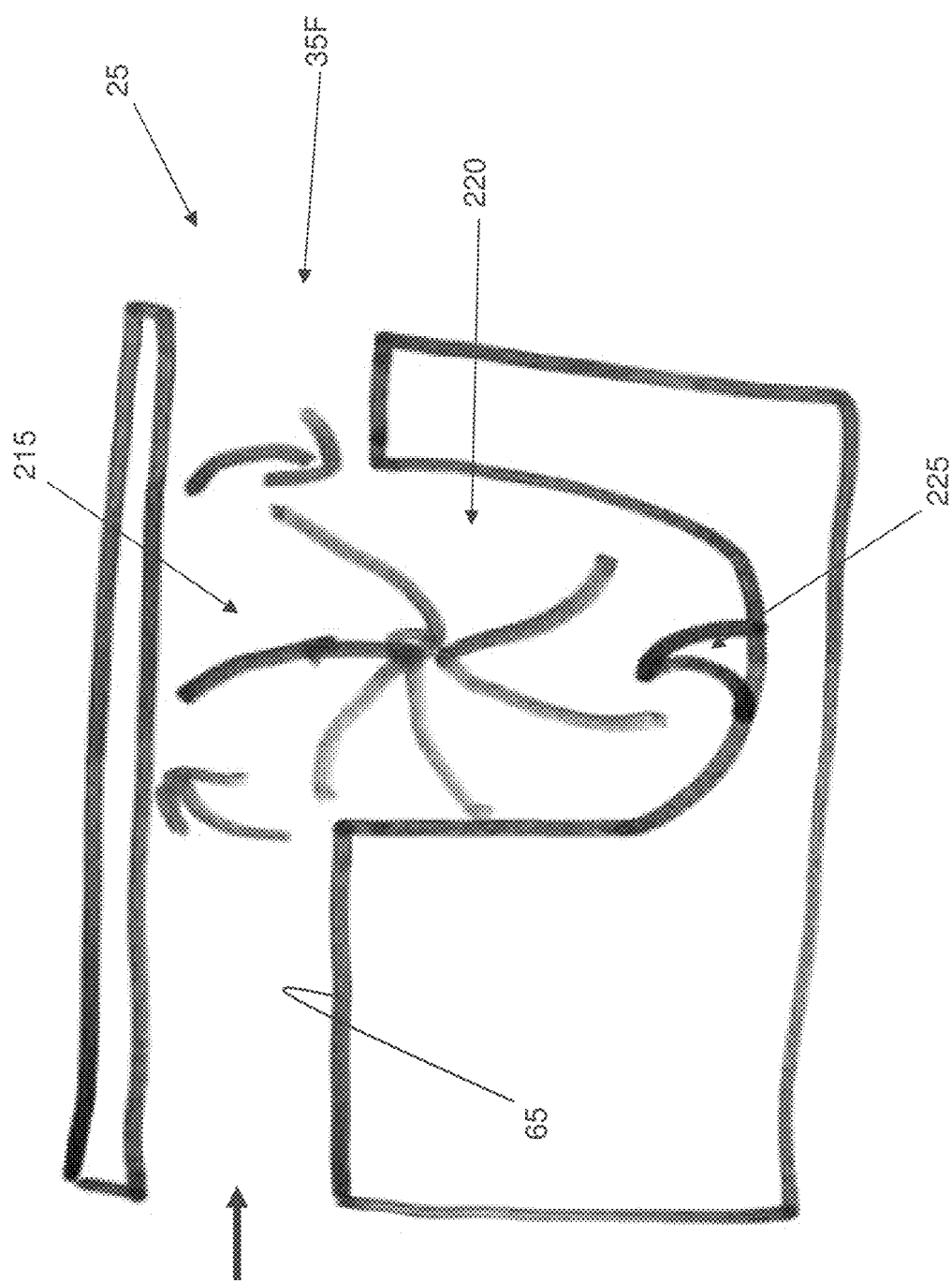

By way of further example but not limitation, and looking now at FIG. 24, there is shown a valve element 35F which comprises a wheel 215 which is configured to rotate in one direction within a chamber 220 when the pressure differential across the valve exceeds a predetermined threshold, whereby to allow fluid flow through lumen 65 of one-way valve 25, but which is prevented from rotating in the opposite direction within the chamber by a stop 225 when the pressure differential across the valve falls below a predetermined threshold, whereby to prevent fluid flow through lumen 65 of one-way valve 25. In this way, valve element 35F provides one-way flow through lumen 65 of one-way valve 25.

It will be appreciated by those skilled in the art that still other configurations are possible for valve element 35.

Alternative Connection Elements

In the foregoing description, one-way valve 25 is described as being having a body 50 which extends through the wall of a blood vessel, and having a proximal connection element 40 contacting the outside surface of the blood vessel, and a distal connection element 45 contacting the inside surface of the blood vessel, and with connection elements 40, 45 being spaced apart from one another such that when one-way valve 25 is deployed across the wall of a blood vessel, the blood vessel wall is captured between proximal connection element 40 and distal connection element 45, whereby to anchor one-way valve 25 in place.

And in the foregoing description, proximal connection element 40 was described as comprising a plurality of legs 80 terminating in a plurality of distally-directed contact surfaces 85, and distal connection element 45 was described as comprising a plurality of legs 90 terminating in a plurality of proximally-directed contact surfaces 95.

However, it should be appreciated that it is possible to anchor one-way valve 25 in place across the wall of a blood vessel using various other configurations of connection elements.

Figure 25:
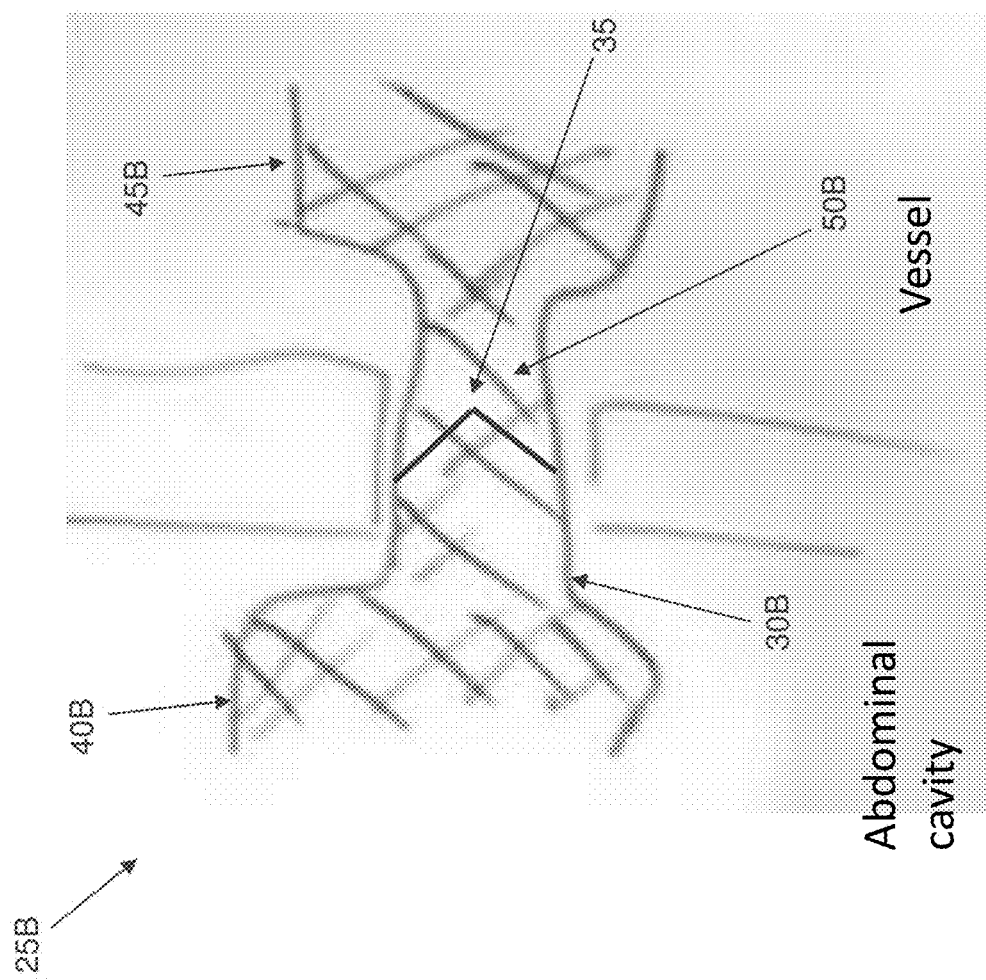
FIGS. 25 and 26 are schematic views which show alternative connection elements which may be used with the novel one-way valve of the present invention.

By way of example but not limitation, and looking now at FIG. 25, in another form of the invention, there is shown a one-way valve 25B having a body 30B, wherein body 30B is in the form of an expandable stent 50B, and having a valve element 35 disposed within body 30B. In this form of the invention, stent 50B is capable of expanding laterally, such that one end of stent 50B forms proximal connection element 40B and the other end of stent 50B forms distal connection element 45B, with proximal connection element 40B contacting the outside surface of the blood vessel and distal connection element 45B contacting the inside surface of the blood vessel, whereby to anchor one-way valve 25B in place. Expandable stent 50B is preferably a covered stent.

Figure 26:
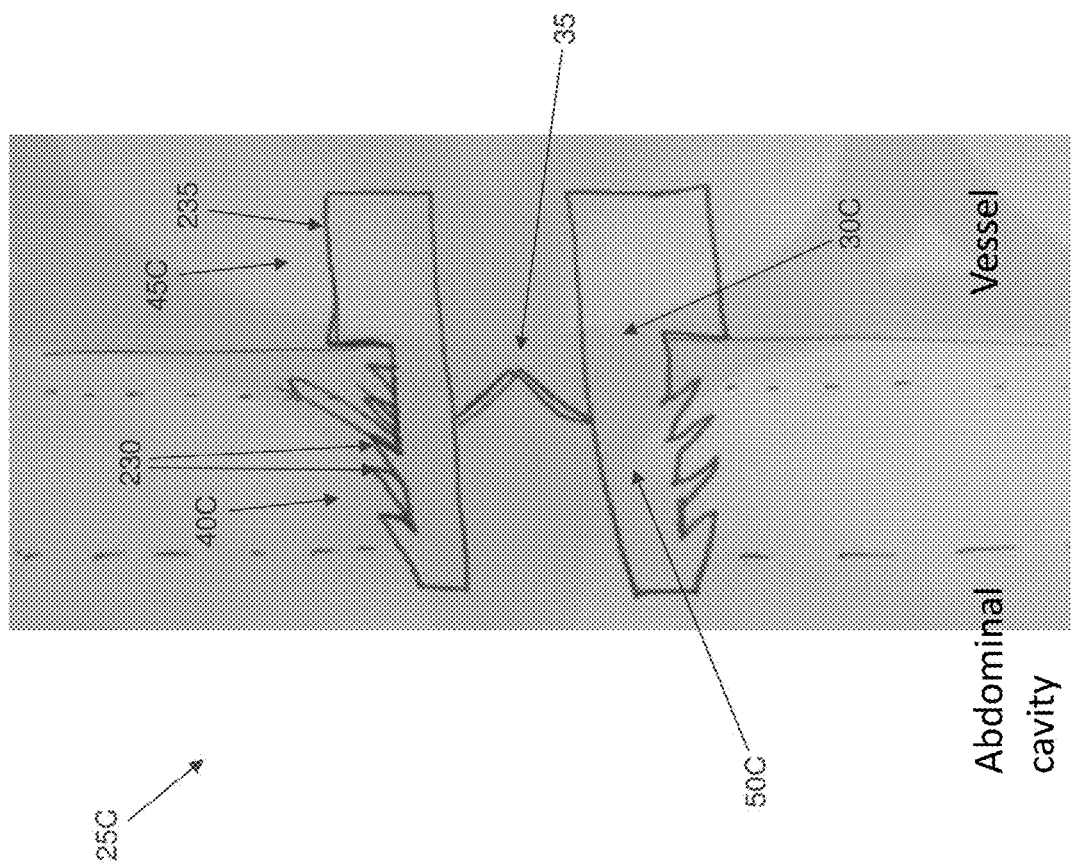

By way of further example but not limitation, and looking now at FIG. 26, in another form of the invention, there is shown a one-way valve 25C having a body 30C, wherein body 30C is in the form of a shaft 50C, and having a valve element 35 disposed within shaft 50C. In this form of the invention, one end of shaft 50C comprises barbs 230 so as to form proximal connection element 40C and the other end of shaft 50C comprises a flange 235 so as to form distal connection element 45C, with proximal connection element 40C engaging the wall of the blood vessel and distal connection element 45C contacting the inside surface of the blood vessel, whereby to anchor one-way valve 25C in place.

It will be appreciated by those skilled in the art that still other configurations are possible for connection elements 40, 45.

Alternative One-Way Valve

Figure 27:
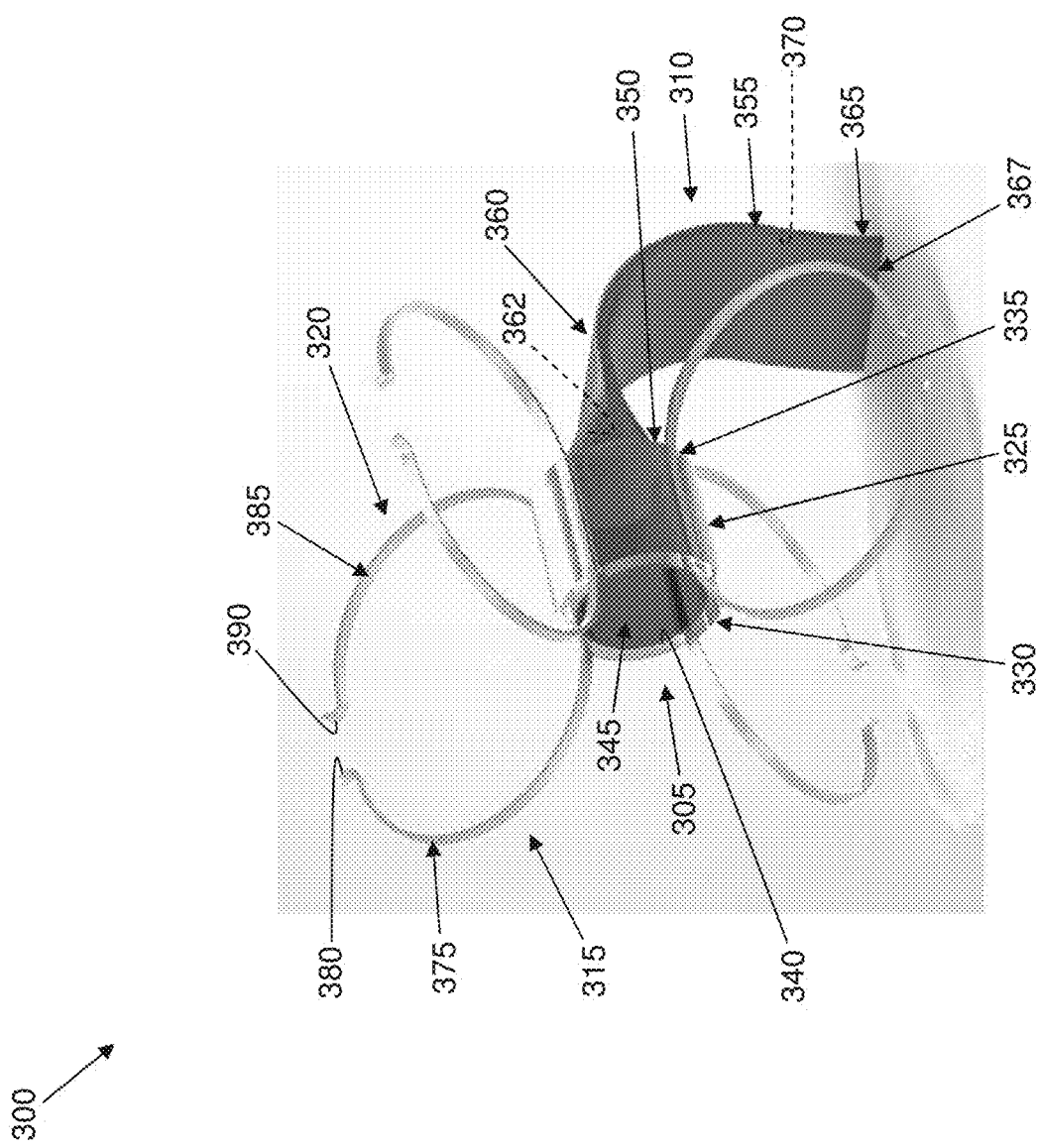
FIGS. 27 and 28 are schematic views showing another novel one-way valve formed in accordance with the present invention.

Looking now at FIG. 27, there is shown another one-way valve 300 formed in accordance with the present invention. One-way valve 300 is generally similar to the one-way valves 25, 25A discussed above, however, the valve element is disposed on the distal end of the one-way valve so that the valve element extends into the blood vessel, as will hereinafter be discussed in further detail.

More particularly, one-way valve 300 generally comprises a body 305, a valve element 310, a proximal connection element 315 and a distal connection element 320.

Body 305 generally comprises a tube 325 having a proximal end 330, a distal end 335, and a lumen 340 extending therebetween. Lumen 340 comprises an inlet 345 disposed at proximal end 330 of tube 325 and an outlet 350 disposed at distal end 335 of tube 325.

In one form of the present invention, tube 325 (and hence, lumen 340) comprises a generally circular cross-section and is radially-compressible in order to aid in implantation of one-way valve 300 into a blood vessel, as will hereinafter be discussed in further detail. It should be appreciated that in a preferred form of the invention, the length of tube 325 can be selected such that the length of tube 325 is at least equal to the thickness of the wall of the blood vessel into which one-way valve 300 is to be implanted, plus the thickness of interstitial tissue which tube 325 will need to extend through. Furthermore, if desired, the diameter of tube 325 can be selected such that tube 325 will comprise a diameter smaller than the diameter of the blood vessel into which one-way valve 300 is to be implanted.

Valve element 310 preferably comprises a flexible length of tubing 355 having a proximal end 360, a distal end 365 and a passageway 370 extending therebetween. Proximal end 360 of tubing 355 comprises a valve element inlet 362 in fluid communication with passageway 370. Tubing 355 is mounted to outlet 350 of lumen 340 such that valve element inlet 362 (and hence, passageway 370) is fluidically connected to lumen 340. Distal end 365 of tubing 355 comprises a valve element outlet 367 in fluid communication with passageway 370. Passageway 370 of tubing 355 is preferably configured such that valve element outlet 367 of passageway 370 is closed (i.e., tubing 355 is flattened) when valve element 310 is in its resting state such that fluid cannot enter into, or exit out of, valve element outlet 367, i.e., such that valve element 310 is "closed". When the pressure differential between (i) the pressure of the fluid entering valve element inlet 362 (which is equal to the fluid pressure entering inlet 345 of lumen 340), and (ii) the pressure of fluid entering valve element outlet 367 of valve element 310 rises above a pre-determined threshold, valve element outlet 367 "opens", whereby to permit fluid to flow from inlet 345, through lumen 340, through outlet 350, through passageway 370 of tubing 355 (i.e., through valve element 310) and out of valve element outlet 367 such that the fluid exits out of one-way valve 300 and into the interior of the blood vessel. By way of example but not limitation, valve element 310 may be configured to "open" (i.e., allow fluid to flow from inlet 345, though lumen 340, through passageway 370 and out valve element outlet 367 of passageway 370) when the pressure differential on the two sides of the valve element is less than 10 mmHg and, more preferably, when the pressure differential is between 2 mmHg and 5 mmHg. It should be appreciated that in this form of the invention, valve element 310 generally comprises a one-way slit-type valve which allows fluid to enter inlet 345, pass through lumen 340, pass through outlet 350 and into passageway 370 of tubing 355 and pass out through valve element outlet 367, but which does not allow fluid to flow in the opposite direction (i.e., from the blood vessel, through valve element 310 and into the abdominal cavity). As a result, when one-way valve 300 is implanted into a blood vessel (e.g., a vein) in the region of the abdominal cavity such that inlet 345 is open to fluid within the abdominal cavity and valve element outlet 367 of valve element 310 is open to the interior of a blood vessel, fluid can flow from the abdominal cavity, through one-way valve 300 and into the blood vessel, but fluid cannot flow in the opposite direction.

In a preferred form of the present invention, tubing 355 of valve element 310 is curved so as to be disposed generally transverse to the longitudinal axis of lumen 340 of body 305 when one-way valve 300 is implanted into the side wall of a blood vessel, and so as to extend along a distance of the blood vessel into which one-way valve 300 is implanted. If desired, tubing 355 of valve element 310 may comprise a smooth outer surface (e.g., Teflon) in order to minimize thrombus formation.

It should also be appreciated that, if desired, an additional valve element (e.g., valve element 35,35A etc.) may be disposed within lumen 340 of body 305 of one-way valve 300 in addition to (or in lieu of) valve element 310. Alternatively, a valve element (e.g., valve element 35,35A, etc.) may be disposed within passageway 370 of tubing 355.

Proximal connection element 315 is preferably mounted to proximal end 330 of tube 325 of valve body 305, and distal connection element 320 is preferably mounted to distal end 335 of tube 325 of valve body 305. Proximal connection element 315 and distal connection element 320 are preferably spaced apart from one another such that when one-way valve 300 is deployed at an internal site (e.g., across the wall of a blood vessel such as a vein), the blood vessel wall is captured between proximal connection element 315 and distal connection element 320, whereby to anchor one-way valve 300 in place within the wall of the blood vessel. To this end, the distance between proximal connection element 315 and distal connection element 320 is preferably equal to the thickness of the vessel wall to be spanned by one-way valve 300 plus any intervening tissue through which the deployed one-way valve 300 will pass (e.g., interstitial tissue, peritoneal layer, etc.).

Proximal connection element 315 preferably comprises a plurality of legs 375 extending radially outward from tube 325 and terminating in a plurality of distally-directed contact surfaces 380. Legs 375 are preferably spring-biased such that they can be radially constrained when one-way valve 300 is being delivered to an internal anatomical site (e.g., via a delivery sheath), and thereafter spring outward (e.g., when the deliver sheath is removed) such that legs 375 and/or distally-directed contact surfaces 380 engage the wall of the blood vessel (or the intervening tissue), whereby to anchor proximal connection element 315 (and hence, one-way valve 300) in position, as will hereinafter be discussed in further detail. In a preferred embodiment of the present invention, one-way valve 300 comprises four legs 375, however, it should be appreciated that one-way valve 300 may comprise a greater number of legs 375 (or a lesser number of legs 375) without departing from the scope of the present invention.

Distal connection element 320 preferably comprises a plurality of legs 385 extending radially outward from tube 325 and terminating in a plurality of proximally-directed contact surfaces 390. Legs 385 are preferably spring-biased such that they can be radially constrained when one-way valve 300 is being delivered to an internal anatomical site (e.g., via a delivery sheath), and thereafter spring outward (e.g., when the delivery sheath is removed) such that legs 385 and/or proximally-directed contact surfaces 390 engage the wall of the blood vessel (or the intervening tissue), whereby to anchor distal connection element 320 (and hence, one-way valve 300) in position, as will hereinafter be discussed in further detail. In a preferred form of the present invention, one-way valve 300 comprises four legs 385, however, it should be appreciated that one-way valve 300 may comprise a greater number of legs 385 (or a lesser number of legs 385) without departing from the scope of the present invention.

In one preferred form of the invention, the distal end of one-way valve 300 (i.e., the portions of the one-way valve which extend into the interior of the blood vessel) are formed so as to be as smooth as possible so as to minimize thrombus formation.

Figure 28:
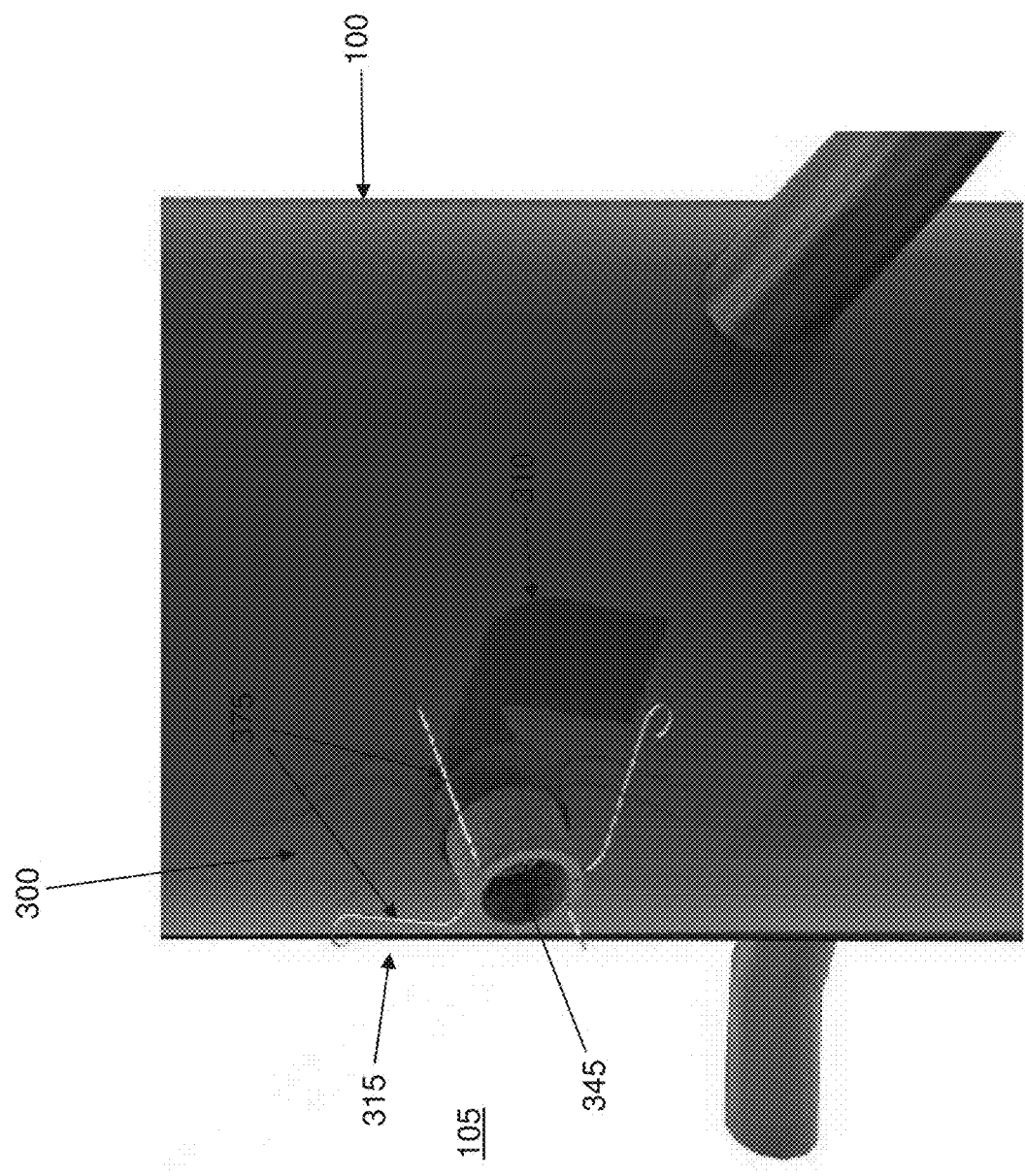
Figure 29:
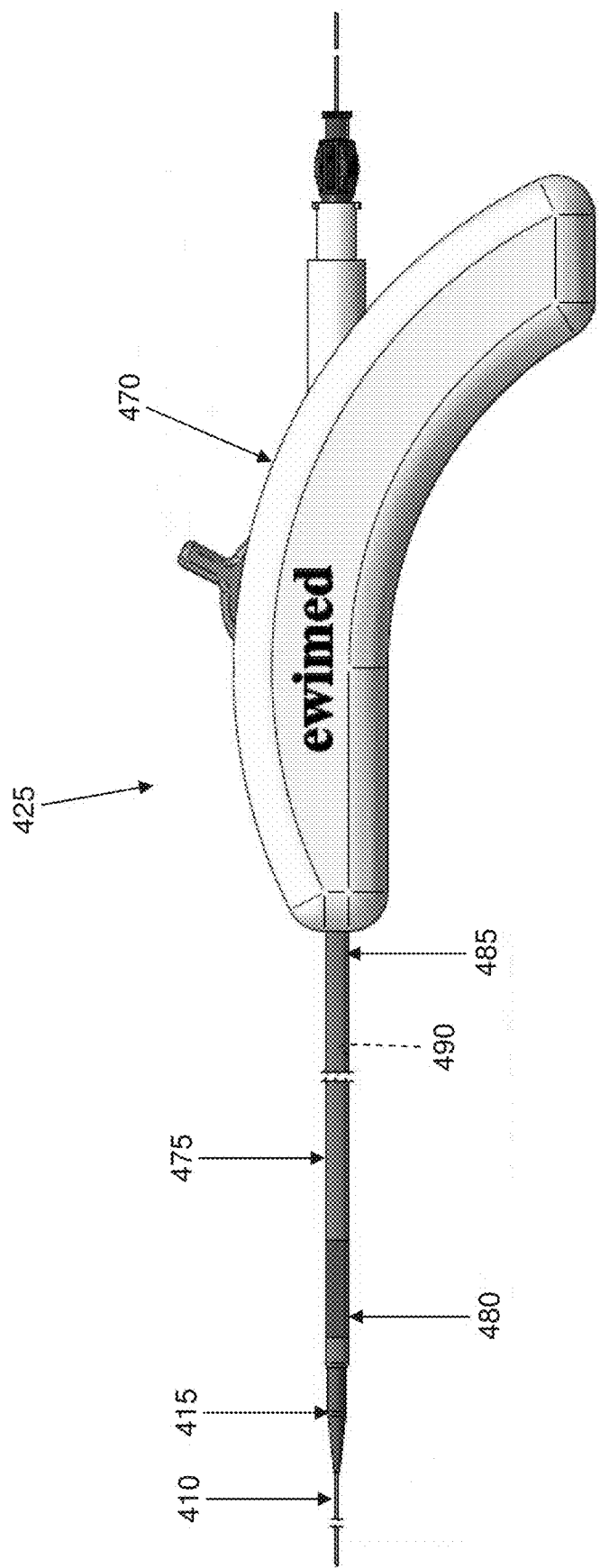

Although one-way valve 300 is depicted in FIGS. 27 and 28 as having two connection elements (i.e., a proximal connection element 315 and a distal connection element 320), it should be appreciated that, if desired, one-way valve 300 may comprise only a single connection element. By way of example but not limitation distal connection element 320 may be omitted. In this form of the invention, proximal connection element 315 is configured to anchor one-way valve 300 in the blood vessel (e.g., proximal connection element 315 might comprise a sewing ring for suturing proximal connection element 315 to the wall of the blood vessel or the intervening tissue). This may be advantageous in some applications, inasmuch as distal connection element 320 would otherwise be disposed within the interior of a blood vessel, and the omission of distal connection element 320 (i.e., legs 385 of distal connection element 320), which is typically disposed within the interior of the blood vessel, can minimize the incidence of thrombosis at the site of implantation.

Exemplary Use of One-Way Valve 300

In use, and looking now at FIG. 28, one-way valve 300 is preferably implanted into the peritoneum/interstitium and the wall of a blood vessel 100 (e.g., the vena cava, the vena iliaca, etc.) such that inlet 345 of one-way valve 300 is in fluid communication with the abdominal cavity 105 (e.g., such that inlet 345 is in fluid communication with the ascetic fluid), and valve element outlet 367 of valve element 310 is in fluid communication with the interior of blood vessel 100. Proximal connection element 315 contacts the outer wall of blood vessel 100 (or contacts the intervening tissue, e.g., the peritoneal layer and/or interstitial tissue), and distal connection element 320 contacts the inner wall of blood vessel 100 such that one-way valve 300 spans the blood vessel wall (and any intervening tissue) and provides a one-way fluid pathway from abdominal cavity 105, through tube 325, through valve element 310 into the interior of blood vessel 100.

As a result, fluid is able to flow from abdominal cavity 105, into inlet 345 of one-way valve 25, through valve element 310 and out valve element outlet 367 of tubing 355 of valve element 310, into the interior of blood vessel 100.

A delivery system (e.g., the aforementioned delivery system 110 or another novel delivery system, as will hereinafter be discussed) may be provided for implanting one-way valve 300 into the wall of a blood vessel.

Although an "endoluminal approach" (e.g., an endovascular approach) is preferably used to implant one-way valve 300 into the side wall of a blood vessel, if desired, an "abdominal approach" may be used.

Alternative Delivery System

As discussed above, one-way valve 300 (or one-way valve 25, 25A, etc.) is configure to be implanted into the side wall of a blood vessel (e.g., a vein) at an internal anatomical site in order to facilitate treatment of ascites. To this end, it is possible to use the novel delivery system 110 discussed above in order to deliver one-way valve 300 to the internal anatomical site and to deploy the one-way valve into the side wall of the blood vessel. However, in one preferred form of the present invention, it is desirable to provide additional control over implanting and deploying one-way valve 300 by utilizing an alternative form of delivery system.

To that end, and looking now at FIGS. 29-36, there is shown an alternative novel delivery system 400 formed in accordance with the present invention. Delivery System 400 generally comprises a puncture device (e.g., the aforementioned puncture device 115), a guidewire 410, a dilator 415, a deployment catheter 420 and a delivery tool 425.

More particularly, the puncture device (not shown in FIGS. 29-36) preferably comprises an elongated shaft having a sharp distal end which may be used to penetrate through tissue (e.g., through the peritoneal layer, through interstitial tissue, through the wall of a blood vessel, etc.). If desired, the puncture device (e.g., puncture device 115) may be omitted, and a guidewire 410 may be used to penetrate tissue.

Guidewire 410 comprises a flexible guidewire of the sort well known in the art which may be used to guide the one-way to an internal site, as will hereinafter be discussed in further detail. If desired, guidewire 410 may comprise a pre-curved tip (FIG. 32) to facilitate addressing the side wall of a blood vessel where one-way valve 300 is to be implanted.

Dilator 415 comprises an elongated tube 430 having a tapered distal end 435. In a preferred form of the present invention, tapered distal end 435 comprises an opening for receiving guidewire 410 so that dilator 415 may be passed over guidewire 410 and advanced to an internal anatomical site, as will hereinafter be discussed in further detail.

Figure 33:
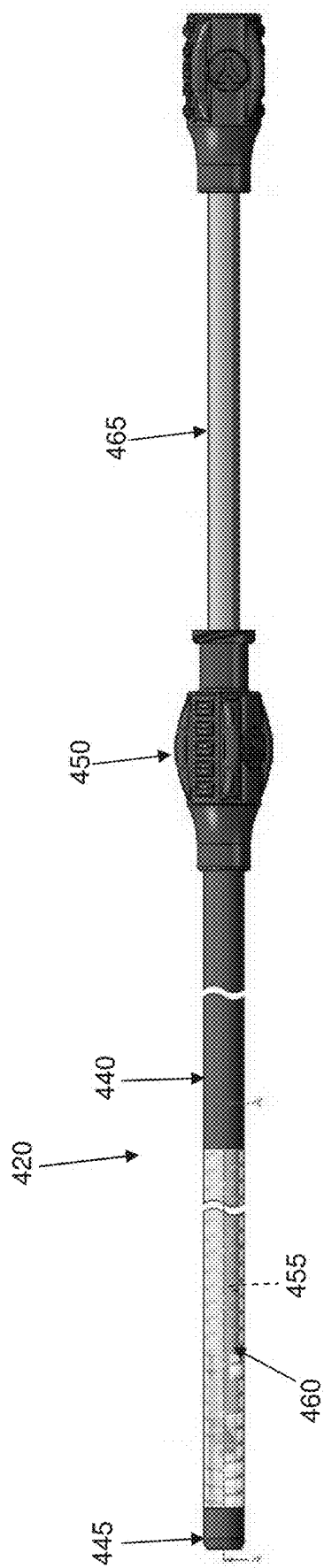
Figure 34:
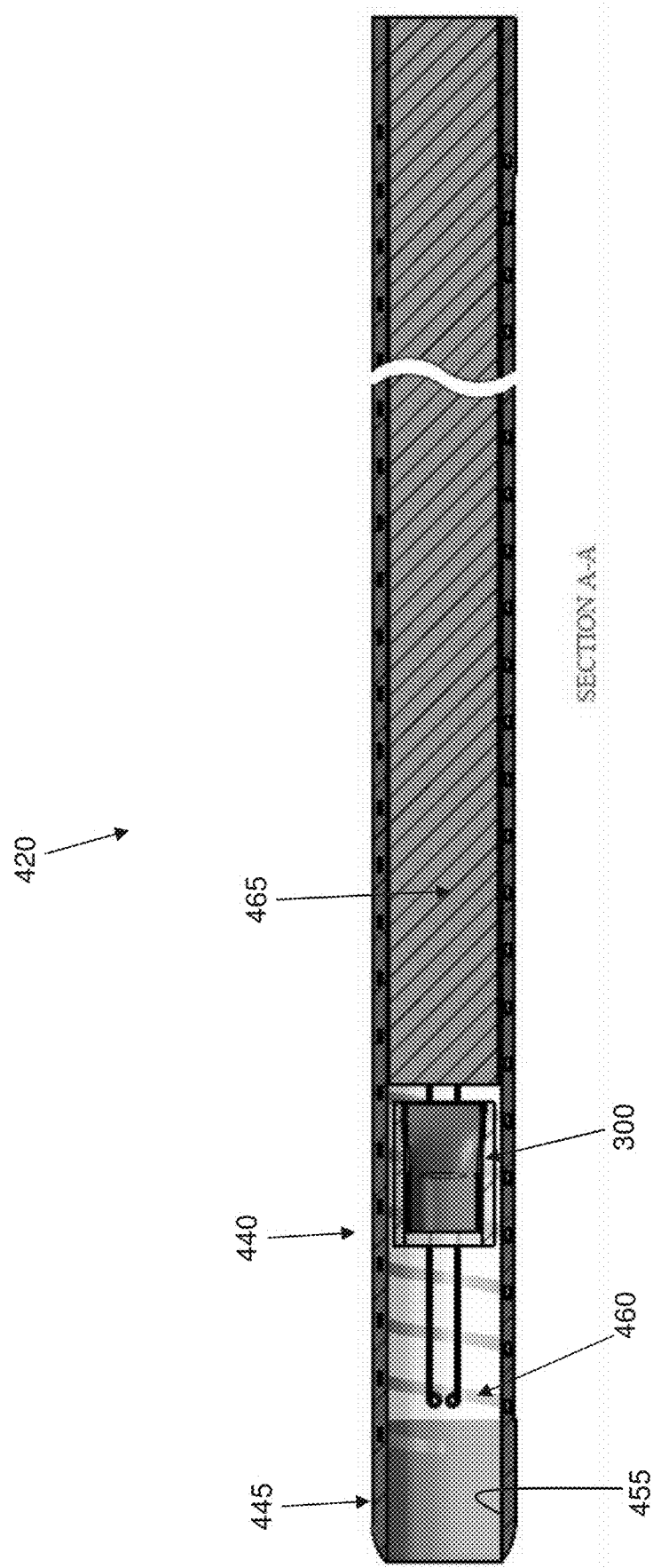

Deployment catheter 420 generally comprises a tube 440 having an open distal end 445, an open proximal end 450, and a lumen 455 extending therebetween (FIG. 33). Lumen 455 of tube 440 is sized so as to hold the one-way valve in a radially-contracted condition, e.g., with the legs of the proximal connection element and the legs of the distal connection element being held parallel to the body of the one-way valve, whereby to provide a reduced profile for delivery of the one-way valve to an internal anatomical site, as will hereinafter be discussed in further detail. In one preferred form of the present invention, deployment catheter 420 also comprises a spring 460 disposed in the distal portion of lumen 455 which biases a push rod 465 (which is slidably disposed within lumen 455) proximally, whereby to prevent premature deployment of the one-way valve out of distal end 445 of deployment catheter 420, as will hereinafter be discussed in further detail.

Delivery tool 425 comprises a handle 470 and a steerable access sheath 475 extending distally from handle 470. Steerable access sheath 475 comprises a flexible distal end 480 and a proximal end 485 mounted to handle 470 with a lumen 490 extending therebetween. A passageway 495 (FIG. 30) is aligned with lumen 490 and extends through handle 470, opening on the proximal end of handle 470. Passageway 495 (and lumen 490) are sized to receive deployment catheter 420, as will hereinafter be discussed in further detail. In a preferred form of the present invention, flexible distal end 480 of steerable access sheath 475 can be selectively articulated using handle 470 by various means, which will be apparent to those skilled in the art in view of the present disclosure.

Method of Implanting and Deploying a One-Way Valve Using Delivery System 400

As discussed above, a one-way valve (e.g., one-way valve 25, 25A, 300, etc.) is intended to be deployed in the side wall of a blood vessel proximate to the abdominal cavity such that fluid can flow from the abdominal cavity, through the one-way valve, and into the interior of the blood vessel. The one-way valve may be deployed at an internal anatomical site using various methods (e.g., open surgery, percutaneous deployment, endoluminal deployment, etc.) or combinations thereof.

For clarity of illustration, implantation of one-way valve 300 using novel delivery system 400 will be discussed hereinbelow in the context of an endovascular approach.

By way of example but not limitation, in order to prepare the internal site for implantation of one-way valve 300, the surgeon first extracts the ascetic fluid from the abdominal cavity (e.g., using a syringe, a collection bag, suction, etc.). If desired, the ascetic fluid may also be drained from the abdominal cavity using an endovascular drain of the sort well known in the art, or by draining the ascetic fluid endovascularly via delivery system 400. The abdominal cavity is then preferably rinsed (e.g., with saline) and drained again.

After the surgeon has located a suitable blood vessel for implantation and identified a suitable implantation site (i.e., a suitable blood vessel for receiving one-way valve 300 proximate to the abdominal cavity), the puncture device (e.g., puncture device 115) is used to puncture the skin of the patient so as to access the interior of a blood vessel. In a preferred form of the invention, access to the vasculature is made by puncturing the jugular vein (FIG. 15A) using puncture device 115 and then the one-way valve is advanced to the selected internal site endoluminally. Alternatively, access to the vasculature may be achieved by puncturing the subclavian vein (also known as the vena subclavia) and then the one-way valve is advanced to the internal site endoluminally. In still another form of the invention, access to the vasculature is made via the vena femoralis (FIG. 15B) at a location remote from the patient's abdomen (e.g., the thigh, groin, etc.) in order to allow endovascular advancement of one-way valve 300 to the selected internal anatomical site.

Steerable access sheath 475 is then advanced into the blood vessel (e.g., the jugular vein) and advanced endovascularly until flexible distal end 480 of steerable access sheath 475 is proximate to the implantation site. The surgeon then selectively articulates flexible distal end 480 of steerable access sheath 475 (e.g., via handle 470) until flexible distal end 480 of steerable access sheath 475 appropriately addresses the side wall of the blood vessel for facilitating implantation of one-way valve 300.

Guidewire 410 is then inserted into passageway 495 of handle 470 and through flexible access sheath 475 and advanced endovascularly until the guidewire is disposed at the internal anatomical site (e.g., the desired location within the inferior vena cava). See FIG. 37. It should be appreciated that, if desired, guidewire 410 may be advanced to the internal anatomical site first, and flexible access sheath 475 can be advanced over the guidewire.

Figure 37:
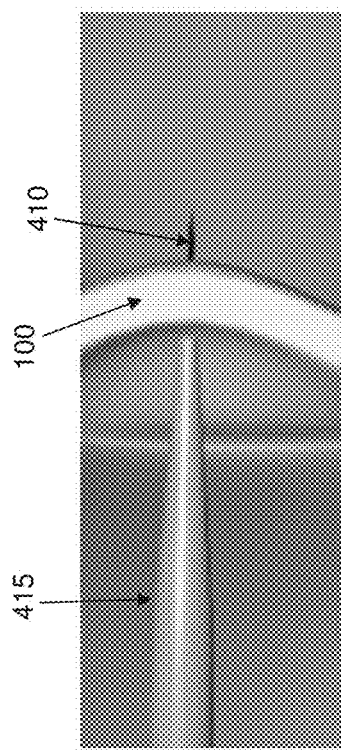
Figure 38:
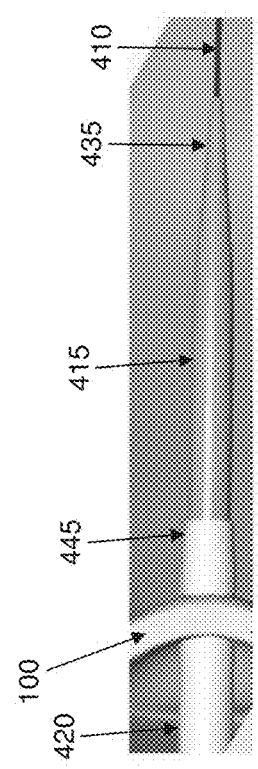

Dilator 415 is then passed over guidewire 410 and advanced to the internal anatomical site (FIG. 37). Tapered distal end 435 of dilator 415 is then passed through the side wall of the blood vessel (and through interstitial tissue, the peritoneal layer, etc.) in order to form an enlarged passageway sized to received one-way valve 300 (FIG. 38).

Figure 39:
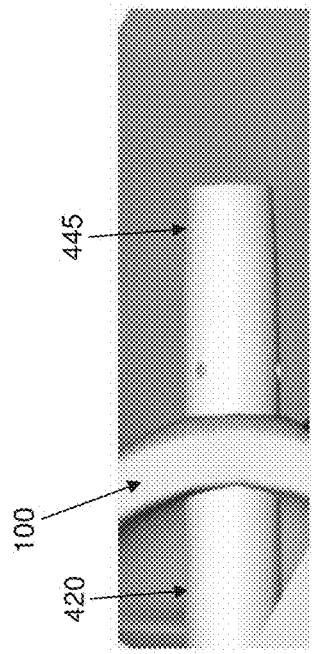
Figure 42:
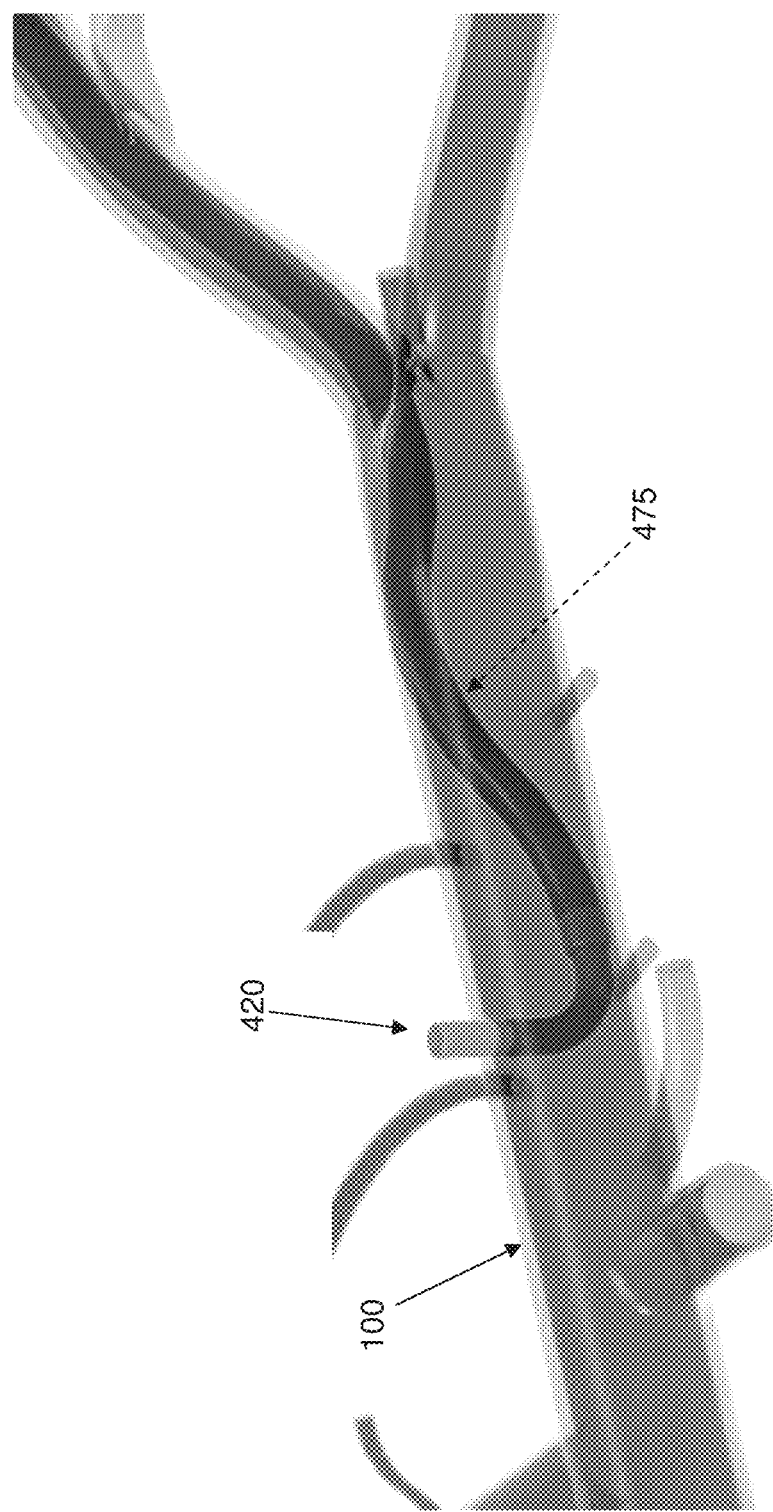

Deployment catheter 420, carrying one-way valve 300 within lumen 455 of the deployment catheter, is then advanced to the internal anatomical site by passing deployment catheter 420 over guidewire 410 and over dilator 415. After distal end 445 of deployment catheter 420 is passed through the side wall of the blood vessel, through the interstitial tissue and through the peritoneal layer, such that distal end 445 is disposed within the abdominal cavity (FIG. 38), dilator 415 and guidewire 410 are removed (i.e., withdrawn proximally) leaving deployment catheter 420 in place within the anatomy (FIG. 39).

It should be appreciated that at this time, one-way valve 300 is disposed just inside the distal end of deployment catheter 420 (or, alternatively, one-way valve 300 may be advanced to a position just inside the distal end of deployment catheter 420). When one-way valve 300 is disposed in the desired position, the surgeon deploys one-way valve 300 by moving pushrod 465 distally against the power of spring 460 such that pushrod 465 engages one-way valve 300 and ejects the proximal end of one-way valve 300 out of deployment catheter 420, such that legs 375 expand radially outward, with distally-directed contact surfaces 380 contacting the outer wall of the blood vessel (or the interstitial tissue covering the outer wall of the blood vessel).

Next, deployment catheter 420 is withdrawn further until distal connection element 320, which is disposed within the interior of the blood vessel (e.g., the interior of the inferior vena cava), is uncovered. As this occurs, radially-constricted legs 385 expand radially outward into their radially-expanded configuration, with proximally-directed contact surfaces 390 contacting the inner wall of the blood vessel. If necessary, steerable access sheath 475 can also be retracted slightly in order to provide room for radial expansion of legs 385. At this point, one-way valve 300 is locked in position within the side wall of the blood vessel. See FIGS. 40 and 41.

Finally, deployment catheter 420 is withdrawn so as to remove the deployment catheter from the patient's body and steerable access sheath 475 is also withdrawn, leaving one-way valve 300 implanted within the side wall of the blood vessel.

At the conclusion of the procedure, one-way valve 300 is securely anchored within the side wall of the blood vessel (e.g., the inferior vena cava), held in position by proximal connection element 315 and distal connection element 320. Inlet 345 of tube 325 of one-way valve 300 is fluidically connected to the abdominal cavity and valve element outlet 367 of tubing 355 of valve element 310 of one-way valve 300 is fluidically connected to the blood vessel (e.g., the interior of the inferior vena cava). As a result, fluid (e.g., fluid resulting from ascites) is able to flow from the abdominal cavity, into inlet 345 of tube 325, along lumen 340 of tube 325, through tubing 355 of valve element 310 and out valve element outlet 367 of tubing 355 into the interior of the blood vessel (e.g., the interior of the inferior vena cava), but fluid is unable to flow in the opposite direction. Thus, fluid can exit the abdominal cavity and enter the blood vessel without the need for a long catheter or the need for external access to the abdominal cavity.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method of treating ascites, the method comprising:
locating and puncturing the side wall of a blood vessel so as to form a puncture site; and
implanting a valve comprising a one-way valve such that the valve is anchored by capturing the blood vessel wall between a proximal connection element and a distal connection element at the puncture site in the side wall of the blood vessel located adjacent the abdominal cavity, so that one side of the valve lies within, and is fluidic ally connected to, the abdominal cavity and the other side of the valve lies within, and is fluidic ally connected to, the interior of the blood vessel, wherein the implanting of the valve allows for fluid resulting from ascites to exit the abdominal cavity and enter the blood vessel without the need for a long catheter or the need for external access to the abdominal cavity; and wherein the blood vessel is one selected from the group consisting of the vena cava inferior and the vena iliaca.

2. A method according to claim 1 wherein the method comprises the step of puncturing the vena cava inferior or vena iliaca and the peritoneal layer of the abdominal cavity.

3. A method according to claim 1 wherein the valve is provided at a location which is infrarenal or suprarenal.

4. A method according to claim 3 wherein the valve is provided at a location which is infrarenal, distal to the inflow of the renal veins.

5. A method according to claim 1 wherein the valve is delivered to the puncture site endoluminally.

6. A method according to claim 5 wherein the method comprises the steps of:
puncturing the jugular vein so as to form a puncture site;
inserting a guidewire into the puncture site at the jugular vein;
advancing the guidewire through the jugular vein and into the vena cava/ilical vein;
passing a delivery sheath over the guidewire;
inserting a puncture device into the vena cava inferior;
puncturing the vena cava/iliacal vein and the peritoneal layer of the abdominal cavity at the same position so as to form an implant site;
advancing a delivery catheter to the implant site;
using the delivery catheter to position the valve at the implant site;
deploying the valve from the delivery catheter into implant site;
removing the delivery catheter and the guidewire; and
removing the delivery sheath.

7. A method according to claim 6 wherein the method further comprises the steps of:
extracting ascetic fluid from the abdominal cavity; and
rinsing the abdominal cavity with a rinsing fluid and draining the rinsing fluid;
wherein these steps are carried out prior to the introduction of the valve to the implant site.

* * * * *